(12) United States Patent
Reed et al.

(10) Patent No.: US 10,203,331 B2
(45) Date of Patent: Feb. 12, 2019

(54) SINGLE CELL DRUG RESPONSE MEASUREMENTS VIA LIVE CELL INTERFEROMETRY

(75) Inventors: Jason C. Reed, Los Angeles, CA (US); Michael A. Teitell, Tarzana, CA (US)

(73) Assignee: The Regents of the University of California, Oakland, CA (US)

( * ) Notice: Subject to any disclaimer, the term of this patent is extended or adjusted under 35 U.S.C. 154(b) by 805 days.

(21) Appl. No.: 14/235,547

(22) PCT Filed: Aug. 2, 2012

(86) PCT No.: PCT/US2012/049388
§ 371 (c)(1),
(2), (4) Date: Jan. 28, 2014

(87) PCT Pub. No.: WO2013/019984
PCT Pub. Date: Feb. 7, 2013

(65) Prior Publication Data
US 2014/0178865 A1 Jun. 26, 2014

Related U.S. Application Data

(60) Provisional application No. 61/514,353, filed on Aug. 2, 2011.

(51) Int. Cl.
*G01N 33/574* (2006.01)
*G01B 11/06* (2006.01)
(Continued)

(52) U.S. Cl.
CPC ..... *G01N 33/57492* (2013.01); *G01B 9/0209* (2013.01); *G01B 9/02057* (2013.01);
(Continued)

(58) Field of Classification Search
None
See application file for complete search history.

(56) References Cited

U.S. PATENT DOCUMENTS

| 5,133,601 A | 7/1992 | Cohen et al. |
| 5,471,303 A | 11/1995 | Ai et al. |

(Continued)

FOREIGN PATENT DOCUMENTS

| CN | 1415067 A | 4/2003 |
| CN | 101313196 A | 11/2008 |

(Continued)

OTHER PUBLICATIONS

Reed et al., "High throughput cell nanomechanics with mechanical imaging interferometry". Nanotechnology, 2008, vol. 19, No. 23, pp. 1-8.
(Continued)

*Primary Examiner* — G Steven Vanni
(74) *Attorney, Agent, or Firm* — Tom Hunter; Weaver Austin Villeneuve & Sampson LLP

(57) ABSTRACT

A central question in cancer therapy is how individual cells within a population of tumor cells respond to drugs designed to arrest their growth. However, the absolute growth of cells, their change in physical mass, whether cancerous or physiologic, is difficult to measure directly with traditional techniques. Embodiments of the invention provide live cell interferometry (LCI) for rapid, realtime quantification of cell mass in cells exposed to a changing environment. Overall, LCI provides a conceptual advance for assessing cell populations to identify, monitor, and measure single cell responses, such as to therapeutic drugs.

14 Claims, 20 Drawing Sheets

(51) Int. Cl.
  *G01B 9/02* (2006.01)
  *G01N 33/50* (2006.01)
(52) U.S. Cl.
  CPC ...... *G01B 9/02089* (2013.01); *G01B 11/0675* (2013.01); *G01N 33/502* (2013.01); *G01N 33/5026* (2013.01)

(56) References Cited

U.S. PATENT DOCUMENTS

| | | |
|---|---|---|
| 6,377,721 B1 | 4/2002 | Walt et al. |
| 6,449,048 B1 | 9/2002 | Olszak |
| 6,858,184 B2 | 2/2005 | Pelrine et al. |
| 7,610,074 B2 | 10/2009 | Boppart et al. |
| 8,524,488 B2 | 9/2013 | Gimzewski et al. |
| 8,599,383 B2 | 12/2013 | Teitell et al. |
| 9,810,683 B2 | 11/2017 | Gimzewski et al. |
| 2002/0196450 A1 | 12/2002 | Olszak et al. |
| 2003/0234936 A1 | 12/2003 | Marron |
| 2004/0058458 A1 | 3/2004 | Anker et al. |
| 2004/0066520 A1 | 4/2004 | Marron |
| 2004/0210289 A1 | 10/2004 | Wang et al. |
| 2004/0218189 A1 | 11/2004 | Izatt et al. |
| 2004/0252310 A1 | 12/2004 | De Lega et al. |
| 2004/0258759 A1 | 12/2004 | Suslick et al. |
| 2005/0057756 A1 | 3/2005 | Fang-Yen et al. |
| 2005/0058990 A1 | 3/2005 | Guia et al. |
| 2005/0088663 A1 | 4/2005 | De Groot et al. |
| 2005/0117165 A1 | 6/2005 | Holbrook et al. |
| 2005/0122527 A1 | 6/2005 | Boccara et al. |
| 2005/0167578 A1 | 8/2005 | Riza et al. |
| 2005/0195405 A1 | 9/2005 | Ina et al. |
| 2005/0200856 A1 | 9/2005 | Groot |
| 2005/0225769 A1 | 10/2005 | Bankhead et al. |
| 2005/0239047 A1 | 10/2005 | Gimzewski et al. |
| 2005/0248770 A1 | 11/2005 | Lin |
| 2006/0291712 A1 | 12/2006 | Popescu et al. |
| 2007/0279638 A1 | 12/2007 | Choo et al. |
| 2008/0018966 A1 | 1/2008 | Dubois et al. |
| 2009/0125242 A1 | 5/2009 | Choi et al. |
| 2009/0163564 A1 | 6/2009 | Borden et al. |
| 2009/0238817 A1 | 9/2009 | Kozlowski |
| 2009/0325211 A1* | 12/2009 | Fang ................... G01N 21/648 435/29 |
| 2010/0079763 A1 | 4/2010 | Arvidson et al. |
| 2010/0284016 A1 | 11/2010 | Teitell et al. |
| 2012/0107840 A1 | 5/2012 | Wagner et al. |
| 2014/0080171 A1 | 3/2014 | Gimzewski et al. |
| 2016/0103118 A1 | 4/2016 | Teitell et al. |
| 2018/0156779 A1 | 6/2018 | Gimzewski et al. |

FOREIGN PATENT DOCUMENTS

| | | |
|---|---|---|
| CN | 101346673 A | 1/2009 |
| EP | 1971690 | 9/2008 |
| EP | 2224946 | 9/2010 |
| EP | 2739937 A1 | 6/2014 |
| JP | 2007-524075 A | 8/2007 |
| JP | 2009-276327 A | 11/2009 |
| JP | 2010-505123 A | 2/2010 |
| JP | 2011-509248 A | 3/2011 |
| WO | WO 01/31286 A2 | 5/2001 |
| WO | WO 2005/001445 A2 | 1/2005 |
| WO | WO 2007/123579 A2 | 11/2007 |
| WO | WO 2008/060369 A2 | 5/2008 |
| WO | WO 2009/086516 A1 | 7/2009 |
| WO | WO 2013/019984 A1 | 2/2013 |
| WO | WO 2014/190303 A1 | 11/2014 |

OTHER PUBLICATIONS

PCT international search report dated Dec. 12, 2012 for PCT application No. PCT/US2012/049388.
U.S. Office Action dated Oct. 7, 2011 issued in U.S. Appl. No. 12/436,702.
U.S. Office Action dated Jul. 20, 2012 issued in U.S. Appl. No. 12/436,702.
U.S. Final Office Action dated Jan. 22, 2013 issued in U.S. Appl. No. 12/436,702.
U.S. Notice of Allowance dated Jul. 30, 2013 issued in U.S. Appl. No. 12/436,702.
U.S. Office Action dated Mar. 29, 2016 issued in U.S. Appl. No. 14/088,992.
PCT International Search Report and Written Opinion dated Sep. 25, 2014 issued in PCT/US2014/039418.
PCT International Preliminary Report on Patentability dated Dec. 3, 2015 issued in PCT/US2014/039418.
European Communication pursuant to Rules 161(2) and 162 EPC dated Jan. 13, 2016 issued in EP 14801181.0.
PCT International Preliminary Report on Patentability dated Feb. 13, 2014 issued in PCT/US2012/049388.
Australian Patent Examination Report No. 1 dated Feb. 12, 2015 issued in AU 2012290024.
Chinese First Office Action dated Nov. 24, 2015 issued in CN 201280048126.5.
European Communication pursuant to Rules 161(2) and 162 EPC dated Mar. 12, 2014 issued in EP 12 819 806.6.
European Extended Search Report dated Mar. 16, 2015 issued in EP 12 819 806.6.
Japanese Office Action dated May 25, 2016 issued in JP 2014-524086.
Balagopalan et al. (Jan. 2011) "Imaging techniques for assaying lymphocyte activation in action," *Nat Rev Immunol*, 11:21-33.
Barer, R. (Mar. 1, 1952) "Interference microscopy and mass determination," *Nature*, 169:366-367.
Davies et al. (Mar. 29, 1952) "Interference microscopy and mass determination," *Nature*, 169:541.
Davies et al. (Sep. 1954) "The Use of the Interference Microscope to Determine Dry Mass in Living Cells and as a Quantitative Cytochemical Method," *Quarterly Journal of Microscopical Science*, 95(part 3):271-304.
Edwards et al. (2011) "T cell recognition of weak ligands: roles of signaling, receptor number, and affinity," *Immunol Res*, 50(1):39-48 [NIH Public Access—Author Manuscript 17pp].
Erskine et al. (2012) "Determining Optimal Cytotoxic Activity of Human Her2neu Specific CD8 T cells by Comparing the Cr51 Release Assay to the xCELLigence System," *Journal of Visualized Experiments and ACEA Biosciences*, 66:e3683 (1-6).
Gamble et al. (Jan. 7, 1960) "Studies in Histochemistry: LVII. Determination of the Total Dry Mass of Human Erythrocyes by Interference Microscopy and X-ray Microradiography," *The Journal of Biophysics and Biochemical Cytology*, 8:53-60.
Gohring et al. (2010) "Label free detection of CD4+ and CD8+ T cells using the optofluidic ring resonator," *Sensors*, 10(6):5798-5808.
Kwong et al. (2009) "Modular nucleic acid assembled p/MHC microarrays for multiplexed sorting of antigen-specific T cells," *J Am Chem Soc*, 131(28):9695-9703.
Ma et al. (Jun. 2011) "A clinical microchip for evaluation of single immune cells reveals high functional heterogeneity in phenotypically similar T cells," *Nature Medicine*, 17(6):738-743.
Mir et al. (2011) "Optical measurement of cycle-dependent cell growth," *Proceedings of the National Academy of Sciences*, 108(32): 13124-13129.
Moore et al. (2004) "Tracking the Recruitment of Diabetogenic $CD8^+$T-Cells to the Pancreas in Real Time," *Diabetes*, 53:1459-1466.
Pittet et al. (2007) "In vivo imaging of T cell delivery to tumors after adoptive transfer therapy," *PNAS*, 104(30):12457-12461.
Reed et al. (2006) "Applications of Imaging Interferometry," *Proceedings of SPIE, The International Society for Optical Engineering*, 0277-786X, 6293:629301-1-629301-8.
Reed et al. (Aug. 14, 2006) "Observation of nanoscale dynamics in cantilever sensor arrays," *NanoTechnology*, 17(15):3873-3879.
Reed et al. (2008) "Live Cell Interferometry Reveals Cellular Dynamism During Force Propagation," *ACS Nano*, 2(5):841-846.

(56) References Cited

OTHER PUBLICATIONS

Reed et al. (Sep. 2011) "Rapid, massively parallel single-cell drug response measurements via live cell interferometry," *Biophysical Journal*, 101:1025-1031.
Stone et al. (2009) "T-cell receptor binding affinities and kinetics: impact on T-cell activity and specificity," *Immunology*, 126(2):165-176.
Tian et al. (2007) "$CD8^+$T cell activation is governed by TCR-peptide/MHC affinity, not dissociation rate," *Journal of Immunology*, 179:2952-2960.
Tzur et al. (2011) "Optimizing optical flow cytometry for cell volume-based sorting and analysis," *PLoS One*, 6(1):e16053 (1-9).
Whiteside, T.L. (2004) "Methods to monitor immune response and quality control," *Dev Biol (Basel)* 116:219-228; discussion 229-236 [Abstract available, 2 pages].
Wooldridge et al. (2009) "Tricks with tetramers: how to get the most from multimeric peptide-MHC," *Immunology*, 126:147-164.
Zangle et al. (Jul. 2013) "Quantifying Biomass Changes of Single CD8+ T Cells during Antigen Specific Cytotoxicity," *PLoS One* 8(7):e68916 (1-8).
U.S. Notice of Allowance dated Jan. 17, 2017 issued in U.S. Appl. No. 14/088,992.
European Extended Search Report dated Nov. 18, 2016 issued in EP 14801181.0.
Chinese Second Office Action dated Jul. 25, 2016 issued in CN 201280048126.5.
Chinese Third Office Action dated Mar. 24, 2017 issued in CN 201280048126.5.
Japanese Decision to Grant Patent dated Apr. 12, 2017 issued in JP 2014-524086.
Hobeika et al. (Jan. 1, 2005) "Enumerating Antigen-Specific T-Cell Responses in Peripheral Blood," *Journal of Immunotherapy*, 28(1): 63-72.
Rathmell et al. (Sep. 1, 2000) "In the Absence of Extrinsic Signals, Nutrient Utilization by Lymphocytes is Insufficient to Maintain Either Cell Size or Viability," *Molecular Cell.*, 6(3): 683-692.
Zangle et al. (Feb. 19, 2014) "High-Throughput Screening of T Cell Cytotoxic Events by Biomass Profiling," *Biophysical Journal 4095-Pos Board B823*, 106(2):811a (1 page).
U.S. Office Action dated Oct. 12, 2017 issued in U.S. Appl. No. 14/890,578.
U.S. Final Office Action dated Jun. 4, 2018 issued in U.S. Appl. No. 14/890,578.
U.S. Notice of Allowance dated May 18, 2017 issued in U.S. Appl. No. 14/088,992.
U.S. Notice of Allowance dated Sep. 11, 2017 issued in U.S. Appl. No. 14/088,992.
Australian Patent Examination Report No. 1 dated Jun. 6, 2017 issued in AU 2016200629.
Canadian First Office Action dated Jun. 5, 2018 issued in CA 2,843,445.
Canadian First Office Action dated Oct. 18, 2017 issued in CA 2,912,842.
Chinese First Office Action dated Jun. 30, 2017 issued in CN 201480029374.4.
Chinese Second Office Action dated Mar. 13, 2018 issued in CN 201480029374.4.
Extended European Search Report dated Jun. 19, 2018 issued in EP 18155863.6.
Japanese Decision to Grant Patent dated May 9, 2018 issued in JP 2017-094485.
Japanese Notice of Reasons for Rejection dated Nov. 20, 2017 issued in JP 2016-515128.
Korean First Office Action dated Jul. 10, 2018 issued in KR 10-2014-7005381.
Korean Notice of Grounds for Rejection dated Mar. 15, 2018 issued in KR 10-2015-7033208.
Rosenberg et al. (Apr. 2008) "Adoptive cell transfer: a clinical path to effective cancer immunotherapy," *Nat Rev Cancer*, 8(4): 299-308 [NIH Public Access—Author Manuscript—22 pages].
Burnes, D (2012) "Quantifying biomass changes of single cells during antigen-specific CD8+ T cell mediated cytotoxicity" *Electronic Thesis and Dissertations UCLA* 33 pages.

\* cited by examiner

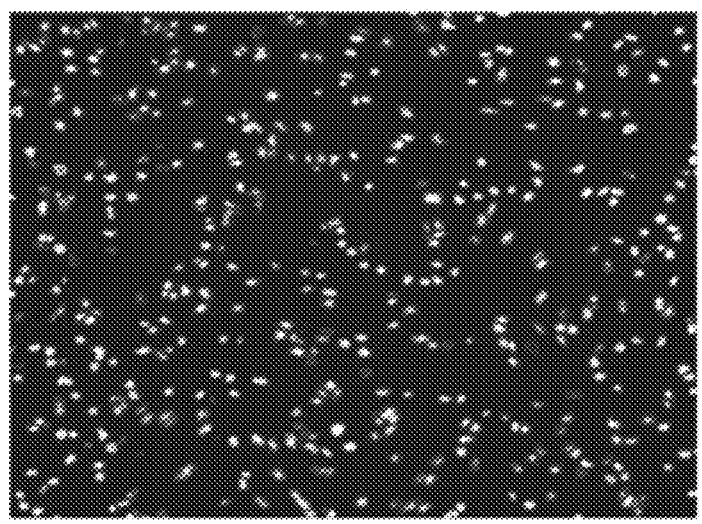
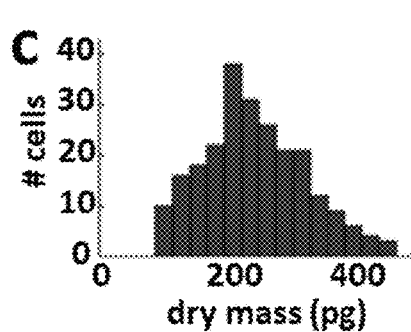
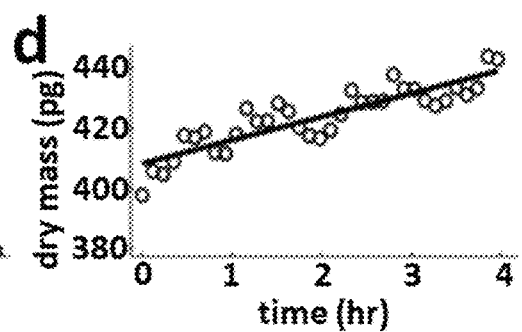
*Fig. 2, cont'd.*

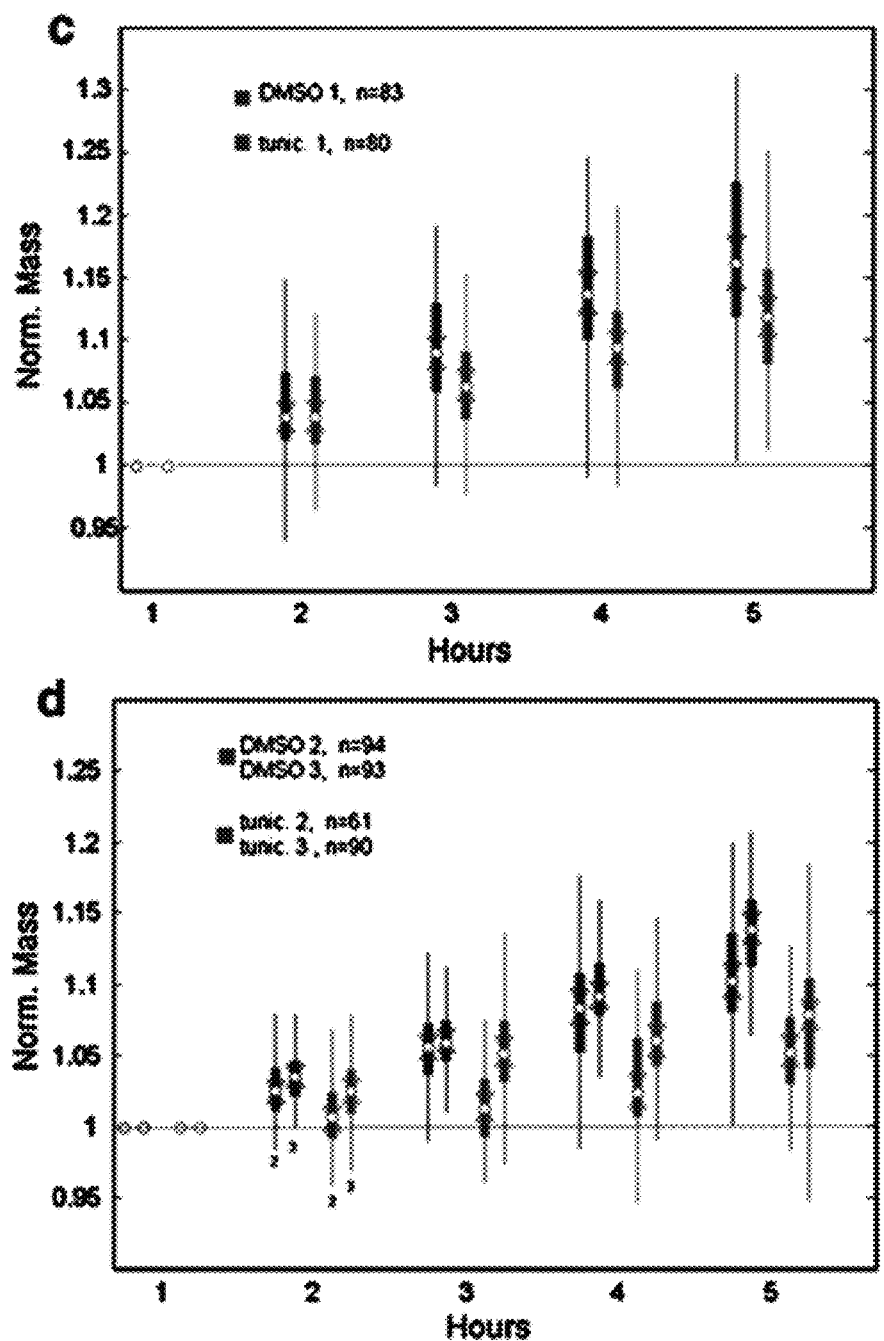
*Fig. 3, cont'd.*

| Cell Line | HER2 status | Herceptin Sensitivity | 7 Day Proliferation Fold Change +/- SEM | 6 Hour Mass Fold Change +/- SEM |
|---|---|---|---|---|
| MCF-7 | HER2 low | Insensitive | 1.13 ± 0.05 | 1.08 ± 0.11 |
| MCA-MB-231 | HER2 low | Insensitive | 0.99 ± 0.05 | 1.01 ± 0.17 |
| SK-BR-3 | HER2 low | Insensitive | 1.45 ± 0.06 | 1.24 ± 0.10 |
| BT-474 | HER2 low | Highly Insensitive | 1.45 ± 0.99 | 1.70 ± 0.39 |

*Fig. 16*

SINGLE CELL DRUG RESPONSE MEASUREMENTS VIA LIVE CELL INTERFEROMETRY

STATEMENT OF GOVERNMENT SUPPORT

This invention was made with Government support under Grant Nos. CA090571, CA107300, and GM074509, awarded by the National Institutes of Health. The Government has certain rights in the invention.

CROSS REFERENCE TO RELATED APPLICATIONS

This application is a U.S. 371 National Phase of PCT/US2012/049388, filed on Aug. 2, 2012, which claims the benefit under 35 U.S.C. Section 119(e) of U.S. Provisional Patent Application Ser. No. 61/514,353, filed on Aug. 2, 2011, entitled "RAPID, MASSIVELY PARALLEL SINGLE-CELL DRUG RESPONSE MEASUREMENTS VIA LIVE CELL INTERFEROMETRY" the contents of all of which are incorporated herein by reference. This application is related to U.S. patent application Ser. No. 12/436,702 filed May 6, 2009, the contents of which are incorporated herein by reference.

TECHNICAL FIELD

The present invention relates to interferometric systems, materials, and techniques that can be used to examine one or more cells.

BACKGROUND OF INVENTION

Interference microscopy provides an interesting biophysical approach to measuring the spatial distribution of material inside cells and other transparent objects. It has been previously shown that an adaptation of this technique, Live Cell Interferometry (LCI), can sensitively detect and track the nanomechanical properties of hundreds of cells simultaneously (1). LCI can also be used to monitor the dynamic flow of the cytoplasm inside single cells as small indentions are made by highly magnetic probes on the surface of a cell (2). Studies showed that an almost instantaneous redistribution of cell material resulted from indentation of the cell surface, which was beyond the detection limit of conventional optical microscopy.

How individual cells regulate their size is poorly understood, as is the relationship between cell mass and well characterized biochemical pathways. While quantitative mass measurements of single live cells began in the 1950s, (3, 4) only recently have newer approaches to increase the speed, precision, and practicality of cellular mass measurements become available. There is a need for new ways to rapidly and simultaneously, measure the masses of one or more cells either alone or clustered within large populations of cells (7, 8). Embodiments of the invention disclosed herein meet this as well as other needs.

SUMMARY OF THE INVENTION

Embodiments of the invention include, for example, interferometry systems, methods and materials that can be used to determine one or more characteristics or properties of one or more cells. Such properties include for example, cell mass, cell volume, optical cell thickness (cell density), and the like. Embodiments of the invention involve observing one or more characteristics or properties of a cell with an interferometer and then using these observations to characterize cellular physiology.

An illustrative embodiment of the invention is a method for observing a mass of a cell using live cell interferometry. Typically, such interferometry methods include the steps of: placing the cell in an observation chamber of an interference microscope adapted to measure a fractional phase shift between a test beam of light and a reference beam of light; exposing the cell to a test beam of light at an illumination wavelength; and then measuring the fractional phase shift between the test beam of light propagating through the cell and a reference/control beam of light. Such measurements can then be used to derive the mass of the cell.

In common embodiments of the invention, the mass of the cell is observed using an equation:

$$m = \frac{1}{\alpha} \int \varphi \lambda dA$$

wherein m is the mass of the cell, $\alpha$ is a constant describing a relationship between the phase shift and cell mass, $\varphi$ is the measured fractional phase shift, $\lambda$ is the illumination wavelength, and integration is performed across an entire cell area, A. In certain embodiments of the invention, $\alpha = 1.8 \times 10^{-3}$ m$^3$kg$^{-1}$. Optionally, the mass of the cell is observed a plurality of times so as to observe how the mass of the cell changes over a period of time. In some embodiments of the invention, the mass of the cell is quantified in real-time. In certain embodiments of the invention, the method is used to quantify the masses of a plurality of cells.

In typical embodiments of the invention, the method is performed using a live cell interferometry system that comprises a detector operatively coupled to the microscope, a sample assembly comprising an observation chamber adapted to contain the cell, a reference assembly comprising a reference chamber adapted to contain the reference cell, and a beam splitter for splitting a light beam from a light source into a test beam and a reference beam. In certain embodiments of the invention, the observation chamber comprises at least one perfusion conduit adapted to circulate a cell medium within the chamber. In some embodiments of the invention, the live cell interferometry system comprises a processor element and a memory storage element adapted to process and store one or more images of the cell(s). In certain embodiments of the invention, the mass property of the cell is observed to quantify a cell's response to a therapeutic agent. Optionally, the one or more cell is obtained from an individual suffering from a cancer and the therapeutic agent is one typically used to treat the cancer (e.g. in methods designed to assess the sensitivity of the cancer cell to the therapeutic agent).

Yet another embodiment of the invention is a method for observing a cellular response to a specific environment or set of environmental conditions, for example a cell culture comprising a test composition, for example a therapeutic agent such as HERCEPTIN. In such methods of the invention, the cell is placed in a first environment (e.g. a first observation chamber) and a mass property of the cell in the first environment is then observed using a process comprising live cell interferometry. In methods of the invention, the mass property observed in the first environment is compared with the mass property of the cell observed in a second environment using a process comprising live cell interferometry. In this way, cellular responses to the first environment can be observed. In typical methods, the first environment comprises a test composition and the second environment does not comprise the test composition. In these methods, the physiology of the cell is transformed by the test composition when the cell is exposed to the test composition in the first environment and this transformation is then observed by the methods of the invention (and typically compared with control cells that are not exposed to the test composition and therefore not transformed by the composition). Optionally, the test composition comprises an antibiotic, an antibody, an alkylating agent, an antimetabolite, a cell cycle inhibitor, a topoisomerase inhibitor, or a cell. In some embodiments of the invention, the test composition functions intracellularly and comprises, for example, an exogenous polynucleotide such as an siRNA.

In certain embodiments of the invention, the cell in which a mass property is observed is present in the first environment as an isolated single cell. Alternatively, the cell in which a mass property can be observed is present in the first environment in a cluster or clump of cells. In some embodiments of the invention, mass properties of a plurality of cells present in the first environment are observed. In embodiments of the invention, the mass property of one or more cells in the first environment can be observed a plurality of times so as to observe how the mass property of the one or more cells changes over a period of time. Optionally, for example, changes in the mass property of the cell are observed over time to observe a temporal mass profile. Certain embodiments of the invention include the steps of comparing an observed temporal mass profile to a database of temporal mass profiles, wherein the database of temporal mass profiles is selected to include temporal mass profiles that are characteristic of cellular sensitivity to the test composition (e.g. in situations where the growth of the cell is inhibited in the presence of a test composition) and temporal mass profiles that are characteristic of cellular resistance to the test composition (e.g. in situations where the growth of the cell is not inhibited in the presence of a test composition).

Other illustrative embodiments of the invention can include, for example, systems and methods for quantifying the mass of a cell and/or observing how the mass of one or more cells changes in response to environmental stimuli. Some embodiments include a method that comprises the steps of: placing one or more cells in an observation chamber of an interference microscope capable of generating and measuring a fractional phase shift between a test beam and a reference beam; exposing the cells to a test beam at an illumination wavelength; measuring the fractional phase shift between the test beam propagating through the cell and a reference beam propagating through a reference cell; and determining the mass of one or more cells with an equation:

$$m = \frac{1}{\alpha} \int \varphi \lambda dA$$

wherein m is the mass of the cell, $\alpha$ is a constant describing a relationship between the phase shift and cell mass, $\varphi$ is the measured fractional phase shift, $\lambda$ is the illumination wavelength, and integration is performed across an entire cell area, A.

Methodological embodiments for observing other cellular properties are also contemplated. For example, in certain embodiments of the invention, the method can be used to observe an optical thickness of a live cell in an aqueous medium. Alternatively, the method can be used to observe a population of live cells simultaneously, for example to identify, monitor, and measure resting and dynamic cell responses to stimuli in a population of live cells. Typically in these methods, the property is observed in response to the cell's exposure to a stimulus such as therapeutic drugs. In certain embodiments, the methods of the invention can be conducted in a highly parallel fashion to profile the differential response of cells in a population to internal or external stimuli. Optionally, the methods further comprise removing the cell from the observation chamber and manipulating the cell for a further analysis. In certain embodiments of the invention, the method is used to obtain information comprising a cell specific profile of a live cell in an aqueous medium and to then store this information in a memory storage element.

A variety of methodological embodiments of the invention are contemplated. For example, certain methodological embodiments of the invention can be performed using a system comprising: a microscope having a Michelson interference objective; a detector such as a camera (e.g. a still camera, a video camera, charge coupled devices (CCD) and the like) operatively coupled to the microscope; a sample assembly comprising an observation chamber adapted to contain the cell; and a reference assembly comprising a reference chamber. Further, such a system may additionally include a memory storage element adapted to store one or more images of the cell and a processor element adapted to process one or more images of the cell. In other embodiments, the microscope is an interference microscope capable of observing interference fringes through a fluid medium. Alternatively, the system is capable of observing interference patterns at multiple phase shifts and then correlating the observed interference patterns to an optical thickness profile of the cell. Such general embodiments are non-limiting as the systems disclosed herein can adopt a variety of configurations. Other embodiments of the invention include a real-time and non-invasive marker of cellular fitness and a method of observing cellular fitness. Such systems and techniques can rely on the observation of changes in cell mass.

Other objects, features and advantages of the present invention will become apparent to those skilled in the art from the following detailed description including the Appendices. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 16 provides a table that illustrates trastuzumab (Herceptin) sensitivity determined by a 7-day proliferation assay (column 3) being shown alongside aLCI mass accumulation profiling data collected at six hours (column 4). HER2 status was determined by O'Brien et al. (see, e.g. Molecular Cancer Therapeutics. 2010, 9, 1489-502).

DETAILED DESCRIPTION OF THE INVENTION

Figure 1:
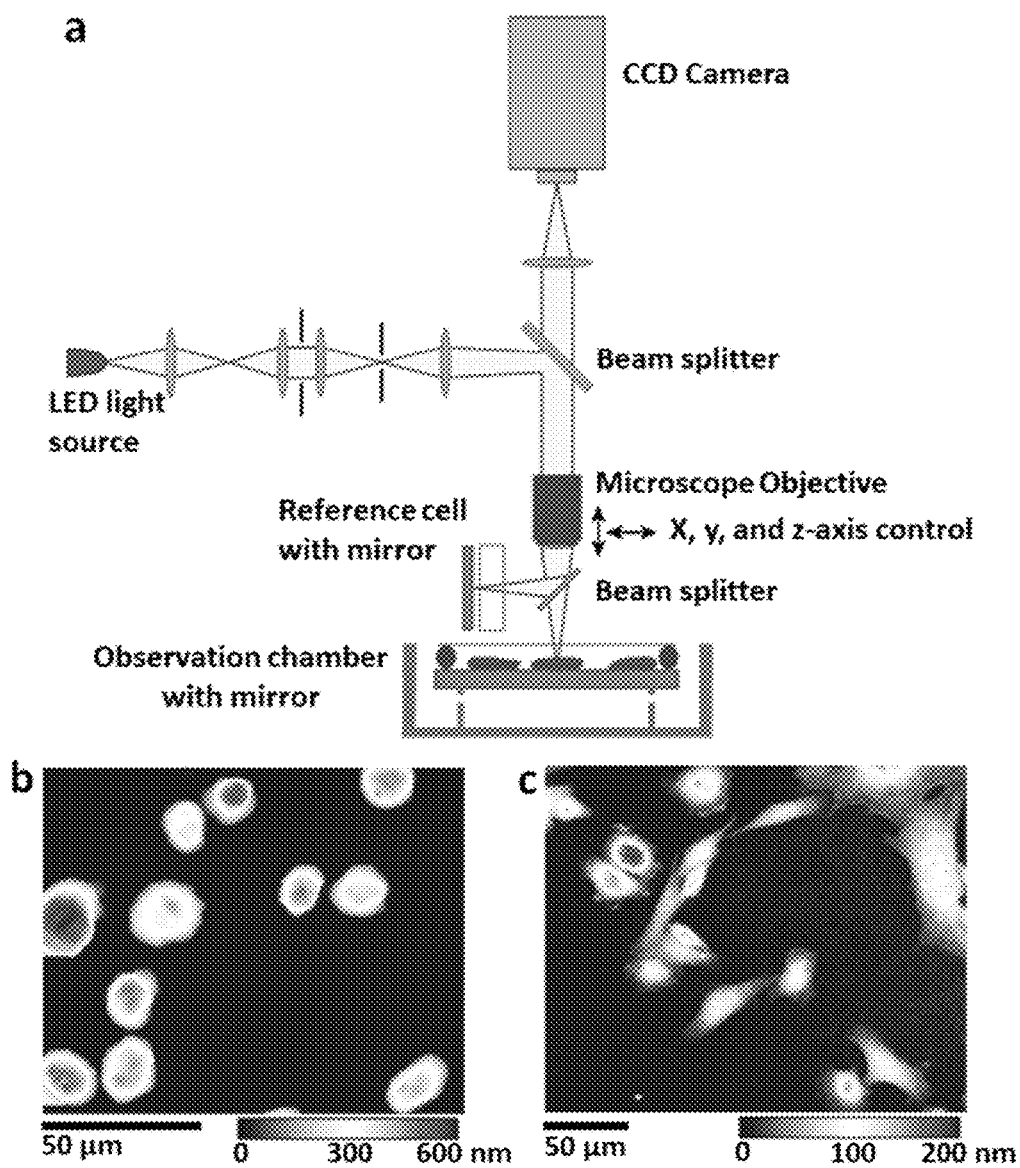
FIG. 1 illustrates a schematic of an embodiment of a live cell interferometer (LCI). The LCI (a) is a Michelson-type interference microscope that compares the optical thickness of a reference cell to the optical thickness of samples placed in the observation chamber. Suspended in the observation chamber is a mirrored substrate, allowing the LCI to make measurements of optical thickness on transparent cells. The relative position of the microscope objective and observation chamber is controlled by computer and translatable in three-dimensions allowing for rapid, automated image acquisition. Throughout data collection, cells in the observation chamber are maintained in standard cell culture conditions (e.g., pH 7.4, 37° C., 5% $CO_2$). The live cell interferometer is capable of measuring the mass of both adherent and non-adherent cells. Frame (b) shows several non-adherent H929 cells attached to the observation chamber substrate after coating the substrate with Poly-L-Lysine solution, while frame (c) shows adherent female Indian Muntjac (9) cells cultured directly on the substrate. The color maps show optical thickness measurements with blue being a low optical thickness relative to background and red being a high optical thickness.

Unless otherwise defined, all terms of art, notations and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims. It must also be noted that as used herein and in the appended claims, the singular forms "a", "and", and "the" include plural referents unless the context clearly dictates otherwise. Thus, for example, reference to "a test composition" includes a plurality of such test compositions and so forth. All numbers recited in the specification and associated claims that refer to values that can be numerically characterized with a value other than a whole number (e.g. the concentration of a compound in a solution) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

The invention disclosed herein has a number of embodiments. Embodiments of the invention provide methods, materials and systems for observing and/or characterizing one or more properties of a cell, for example its mass and/or how the mass of a cell changes in response to various environmental conditions. Illustrative embodiments of the invention comprise using interferometry to obtain information on the mass of a cell and/or characterize one or more cellular properties that are related to the mass of a cell. Illustrative cellular properties that can be observed by embodiments of the invention can include for example cytoskeletal remodeling behavior in response to a stimulus, for example a stimulus comprising exposure to a drug or other biologically active agent as well as a variety of other factors. In some embodiments of the invention, the phenomena that is observed is one corresponding to, or associated with, a pathological condition such as aberrant cell division, such as that occurring in precancerous and cancerous cells. In some embodiments of the invention, the cell membrane in which movement is observed is a membrane of a single cell. In other embodiments of the invention, the membrane properties of a plurality of cells are observed. In certain embodiments, the membrane is a membrane of a cell in a tissue. In other embodiments, the membrane is a membrane of a cell within a colony of cells (e.g. an in vitro cell culture of primary cells taken from a patient or an established cell line). In typical embodiments of the invention, the cell is a eukaryotic (e.g. mammalian) cell.

In typical interferometric embodiments of the invention, an interferometer uses, for example, a Michelson configuration. In addition, methods and elements associated with interferometric technologies including spectrally resolved interferometry, wavelength scanning interferometry, digital holography and the like can be used in embodiments of the invention. While many interferometric microscopy systems and methods can be adapted for use with embodiments of the invention, other embodiments of the invention can use scanning optical microscopes, confocal microscopes and the like. An illustrative and non-limiting list of publications that describe optical profiling methods and materials that can be adapted for use with embodiments of the invention are disclosed for example in U.S. Patent Application Nos. 20100284016; 20050248770; 20050225769; 20050200856; 20050195405; 20050122527; 20050088663; 20040252310; 20050117165; 20030234936; 20040066520; 20080018966 and 20050167578, the contents of which are incorporated by reference.

Embodiments of the invention use optical profilometry techniques to provide for example methods of height measurement, shape measurement, as well as measures of other modulations in the shapes of cell membranes and other properties that can relate to the mass of a cell. Depending on the shape, size etc. of a test cell or a population off cells, these techniques typically use structured light, focusing properties of optics, interference of light, etc., to optimize results in an economical and practical way. Moire' techniques, ESPI (electronic speckle-pattern interferometry), laser scanning, photogrammetry, and interferometry are illustrative techniques developed for conducting three-dimensional shape measurements. The technique of white-light vertical scanning interferometry (VSI), also commonly referred to as white-light interferometry or coherence radar, is used for imaging small objects, typically those with roughness that does not exceed a few micrometers. VSI methodology is based on detection of the coherence peak created by two interfering, polychromatic wavefronts. It has many advantages such as absolute depth discrimination, fast measurement cycle, and high vertical resolution. One advantage of VSI is the ease with which it can be combined with other measurement techniques, such as phase-shifting interferometry (PSI), which are superior in accuracy but may lack the scanning depth of VSI. PSI is typically used for measurements of smooth surfaces with small changes in profile (see K. Creath, "Temporal Phase Measurement Methods," Interferogram Analysis, Institute of Physics Publishing Ltd., Bristol, 1993, pp. 94-140). VSI is generally used to measure smooth and/or rough surfaces with large interpixel height ranges (K. G. Larkin, "Efficient Nonlinear Algorithm for Envelope Detection in White Light Interferometry," J. Opt. Soc. Am., A/Vol. 13, 832-843 (1996). The combination of VSI and PSI has been used, for example, to measure large steps with PSI precision (C. Ai, U.S. Pat. No. 5,471,303). The PSIOTF technique, which is a particular case of VSI and PSI combination, improves measurements of smooth surfaces in the larger height range (see, e.g. Harasaki et al., "Improved Vertical Scanning Interferometry," Appl. Opt. 39, 2107-2115, 2000). Typical VSI and PSI systems and methods are disclosed for example in U.S. Pat. Nos. 5,133,601, 5,471,303 and U.S. Pat. No. 6,449,048, and U.S. Patent Application No. 20020196450, the contents of which are incorporated by reference.

As noted above, embodiments of the invention include methods for observing a mass property of a cell using the systems disclosed herein. Embodiments include for example observations of membranes where membrane motion is observed with real-time phase measurements of factors such as optical cell thickness (cell density), cell volume and the like. One such method is a method for observing a property of a cell (and/or a population of cells), the method comprising placing the cell in a cell observation chamber of an optical microscope having a Michelson interference objective; and using this Michelson interference objective to observe the cell. Typically in such embodiments, a mass property can be correlated to an observable property of the cell such as cell density and/or cell volume and the like, and in this way the methods allow a mass property of the cell to be observed.

One illustrative embodiment of the invention is method for observing a mass of a cell using live cell interferometry. Typically, such methods include the steps of: placing the cell in an observation chamber of an interference microscope adapted to measure a fractional phase shift between a test beam of light and a reference beam of light; exposing the cell to a test beam of light at an illumination wavelength; and then measuring the fractional phase shift between the test beam of light propagating through the cell and the reference beam of light (e.g. one propagating through a control or reference cell). In some embodiments of the invention, artisans can use the microscope to measure the fractional phase shift between the test beam propagating through the cell and the reference beam propagating through the reference cell, wherein the fractional phase shift correlates to a property of the cell. Such measurements can then be used to derive the mass of the cell.

In common embodiments of the invention, the mass of the cell is observed/derived using an equation:

$$m = \frac{1}{\alpha} \int \varphi \lambda dA$$

wherein m is the mass of the cell, $\alpha$ is a constant describing a relationship between the phase shift and cell mass, $\varphi$ is the measured fractional phase shift, $\lambda$ is the illumination wavelength, and integration is performed across an entire cell area, A. In certain embodiments of the invention, $\alpha=1.8 \times 10^{-3}$ m$^3$ kg$^{-1}$. Optionally, the mass of the cell is observed a plurality of times so as to observe how the mass of the cell changes over a period of time. In some embodiments of the invention, the mass of the cell is quantified in real-time. In certain embodiments of the invention, the method is used to quantify the masses of a plurality of cells.

In typical embodiments of the invention, the method is performed using a live cell interferometry system that comprises a detector operatively coupled to the microscope, a sample assembly comprising an observation chamber adapted to contain the cell, a reference assembly comprising a reference chamber adapted to contain the reference cell, and a beam splitter for splitting a light beam from a light source into a test beam and a reference beam. In certain embodiments of the invention, the observation chamber comprises at least one perfusion conduit adapted to circulate a cell media within the chamber. In some embodiments of the invention, the live cell interferometry system comprises a processor element and a memory storage element adapted to process and store one or more images of the cell. In certain embodiments of the invention, the mass of the cell property (e.g. the mass of the cell, the weight of the cell, the volume of a cell etc.) is observed to quantify a cell's response to a therapeutic agent. Optionally for example, the cell is obtained from an individual suffering from a cancer and the therapeutic agent is used to treat the cancer.

Yet another embodiment of the invention is a method for observing a cellular response to a specific environment, for example one comprising a therapeutic agent such as HERCEPTIN. In such methods of the invention, the cell is placed in a first environment and a mass property of the cell in the first environment is then observed using a process comprising live cell interferometry. Typically this comparison comprises observing cells of the same lineage (e.g. a cancer lineage) derived from the patient in the first and second environments. In this way, cellular responses to the first environment and/or second environment can be observed. Typically in these methods, the first environment comprises a test composition and the second environment does not comprise the test composition. Optionally, the test composition comprises an antibiotic, an antibody, an alkylating agent, an antimetabolite, a cell cycle inhibitor, a topoisomerase inhibitor, an siRNA or a cell (e.g. a human immune cell such as an antigen presenting cell). In these methods, the mass property observed in the first environment is compared with the mass property of the cell observed in a second environment using a process comprising live cell interferometry.

In certain embodiments of the invention, the cell in which a mass property is observed is present in the first environment as an isolated single cell. Alternatively, the cell in which a mass property can be observed is present in the first environment in a cluster or clump of cells (e.g. an aggregation of at least 5, 10, 15, 20, 25, 30, 35, 40, 45 or 50 cells). In some embodiments of the invention, mass properties of a plurality of cells present in the first environment are observed. In embodiments of the invention, the mass property of one or more cells in the first environment can be observed a plurality of times so as to observe how the mass property of the one or more cells changes over a period of time. Optionally, for example, changes in the mass property of the cell are observed over time to observe a temporal mass profile (e.g. the specific way in which the cell's mass changes over a period of time). Certain embodiments of the invention include the steps of comparing an observed temporal mass profile to a database of temporal mass profiles, wherein the database of temporal mass profiles is selected to include temporal mass profiles that are characteristic of cellular sensitivity to the test composition and temporal mass profiles that are characteristic of cellular resistance to the test composition.

Other illustrative embodiments of the invention can include, for example, systems and methods for quantifying the mass of a cell and/or observing how the mass of one or more cells changes in response to environmental stimuli. Some embodiments include a method that comprises the steps of: placing one or more cells in an observation chamber of an interference microscope capable of generating and measuring a fractional phase shift between a test beam and a reference beam; exposing the cells to a test beam at an illumination wavelength; measuring the fractional phase shift between the test beam propagating through the cell and a reference beam propagating through a reference cell; and determining the mass of one or more cells with an equation:

$$m = \frac{1}{\alpha} \int \varphi \lambda dA \qquad (1)$$

wherein m is the mass of the cell, α is a constant describing a relationship between the phase shift and cell mass, φ is the measured fractional phase shift, λ is the illumination wavelength, and integration is performed across an entire cell area, A.

Methodological embodiments for observing mass and/or other cellular properties are contemplated. For example, in certain embodiments of the invention, the method can be used to observe an optical thickness of a live cell in an aqueous medium. Alternatively, the method can be used to observe a population of live cells simultaneously, for example to identify, monitor, and measure resting and dynamic cell responses to stimuli in a population of live cells. Typically in these methods, the property is observed in response to the cell's exposure to a stimulus such as therapeutic drugs. In certain embodiments, the methods of the invention can be conducted in a highly parallel fashion to profile the differential response of cells in a population to internal or external stimuli. Optionally, the methods further comprise removing the cell from the observation chamber and manipulating the cell for a further analysis. In certain embodiments of the invention, the method is used to obtain information comprising a cell specific profile of a live cell in an aqueous medium and to then store this information in a memory storage element.

A variety of methodological embodiments are contemplated. For example, certain methodological embodiments of the invention can be performed using a system comprising: a microscope having a Michelson interference objective; a detector such as a camera (e.g. a still camera, a video camera, charge coupled devices (CCD) and the like) operatively coupled to the microscope; a sample assembly comprising an observation chamber adapted to contain the cell; and a reference assembly comprising a reference chamber. Further, such a system may additionally include a memory storage element adapted to store one or more images of the cell and a processor element adapted to process one or more images of the cell. In other embodiments, the microscope is an interference microscope capable of observing interference fringes through a fluid medium. Alternatively, the system is capable of observing interference patterns at multiple phase shifts and then correlating the observed interference patterns to an optical thickness profile of the cell. Such general embodiments are non-limiting as the systems disclosed herein can adopt a variety of configurations. Other embodiments of the invention include a real-time and non-invasive marker of cellular fitness and a method of observing cellular fitness. Another embodiment of the invention is a system for observing a property of a cell's mass comprising: a microscope; a detector such as a point detector, a line detector, a microbolometer or a camera (e.g. a still camera, a video camera, charge coupled devices (CCD) other image capture devices used microscopy) operatively coupled to the microscope; a sample assembly comprising an observation chamber adapted to contain the cell; and a reference assembly comprising a reference chamber. Such systems and techniques rely on the observation of changes in cell mass.

Other embodiments of the invention include a system for obtaining one or more images of a cell comprising: an interference microscope capable of extracting information from interferometric fringes; a detector operatively coupled to the interference microscope; a sample assembly comprising an observation chamber adapted to contain the cell, and a reference assembly adapted to substantially match an optical path length of the sample assembly. One typical embodiment of the invention is a system for obtaining an image of a cell comprising: a microscope having a Michelson interference objective; a camera operatively coupled to the microscope; a sample assembly comprising an observation chamber adapted to contain the cell; and a reference assembly comprising a reference chamber adapted to contain a fluid (e.g. the media disposed in the observation chamber, RPMI, PBS, water or the like).

Embodiments of the system are adapted to use a variety elements and methods known in the art and/or described herein. For example, while the sample and/or reference chambers typically include a fluid, other embodiments that do not need a fluid cell, e.g. a transmissive media (TTM) objective (e.g. by using a salt) can also be used in embodiments of the invention. Moreover, in certain embodiments of the invention, the sample chamber that holds the cell is closed while in other embodiments the cell chamber can be open on top (i.e. does not need a lid). Embodiments of the invention can include matching the optical path difference between the arms of an interferometric system, typically by controlling the sizes and architecture of the elements that make up the sample and reference assemblies. For example, in certain embodiments of the invention, the reference assembly further comprises: a first optical window; a first housing element adapted to hold the first optical window; a second optical window; a second housing element adapted to hold the second optical window; and a plurality of spherical spacer elements disposable between the first optical window and the second optical window and adapted to separate the first and second optical windows to a defined distance. This is merely an illustrative and non-limiting example of one way of accomplishing this goal, and there are a variety of other ways to match the optical path difference between the arms etc. (e.g. in an embodiment where just one plate that matches the cell chamber, two wedges can be shifted with respect to each other so that the optical path is varied, different types of spacers can be used instead of spherical spacer elements, etc.).

Another embodiment of the invention includes the steps of providing an interferometer comprising a beam splitter, reference mirror and compensating fluid cell, wherein said fluid cell is used to adjust for optical path differences induced by fluid surrounding the specimen. Such methods can comprise using a piezoelectric translator to decrease the light path a small amount causing a phase shift between the test and reference beams. Such methods can comprise determining the variation in phase imparted to light propagating through a transparent cell body. Such methods can comprise determining the cell mass in relation to the measured phase retardation with the formula:

$$m = \frac{1}{\alpha} \int \varphi \lambda dA$$

Wherein m is the mass of the cell, α is a constant describing the relationship between phase shift and cell mass, φ is the measured fractional phase shift, λ is the illumination wavelength, and integration is performed across the entire cell area, A Embodiments of the invention include a variety of permutations of these systems. For example, in certain embodiments, the observation chamber comprises at least one perfusion conduit adapted to circulate a cell media within the chamber. Some embodiments of the invention further comprise a processor element and a memory storage element adapted to process and store one or more images of the cell. In certain embodiments of the invention, the cell is labelled with another marker/probe known in the art such as a fluorescent marker (e.g. green fluorescent protein) and the system includes optical elements adapted to image these labelled cells. Some embodiments of the invention include additional elements used to observe cellular properties such as devices and processes (e.g. software based processes) used in FT infrared spectroscopy, Raman spectroscopy and the like.

The methods of the invention can be used to obtain a wide variety of information relating to one or more cellular properties. For example, in certain embodiments of the invention, the method can be used for example to observe an optical thickness of a live cell in an aqueous medium. Embodiments of the invention can be used to measure the optical thickness of a live cell in liquid (i.e. culture medium) to 1 nm vertical resolution with an image capture rate of 1 every 11 secs (can be increased to 1 in 1/1000th of a second with modifications) for all cells in the field of view. This observation provides useful information and comprises, for example, a measure of the proteins, nucleic acids and other molecules in the cell that retard the return of the interferometer light back to the CCD detector camera on a pixel-by-pixel basis across the horizontal axis of a cell body within the field of view.

Alternatively, the method can be used to observe a cell mass property of a live cell in an aqueous medium. For example, cell mass in liquid can be calculated for each cell from observations obtained from embodiments of the systems disclosed herein. By collecting such calculations over a period of time, adaptive and/or maladaptive changes in cell optical thickness (mass) can be evaluated in response to environmental (i.e. interactions with other cells such as antigen presenting cells, interactions with agents such as HERCEPTIN or the like). From this information, one can then, for example, derive biophysical parameters for each cell in the field, such as viscoelasticity (typically using calculations known in the art). In this way, artisans can observe cell mass properties under changing conditions over time. In yet another embodiment of the invention cell mass "signatures" can be derived for each individual cell in a population at rest or in response to some environmental condition. In another embodiment of the invention, individual live cells with unique properties can be isolated and recovered from the field of view because their position(s) are identified in the interferometer field of view. Further manipulations such as recovering an observed cell for additional analyses are contemplated. Recovery can be with a suction pipette, for example, to allow further studies (i.e. adoptive transfer into small animals, further testing in a variety of settings, such as single cell microarray gene expression profiling etc.).

As noted above, in some embodiments of the invention, the method is used to observe a mass property of a live cell in an aqueous medium. Optionally, the method is used to observe a population of live cells, for example to observe resting and dynamic responses to stimuli in a population of live cells. In certain embodiments of the invention, resting and/or dynamic responses of a plurality of cells in a population of live cells can be measured simultaneously. Typically in these methods, the property is observed in response to the cell's exposure to a stimulus such as a composition introduced into the cell's media. Optionally the methods further comprise removing the cell from the observation chamber and manipulating the cell for a further analysis. In certain embodiments of the invention, the method is used to obtain information comprising a cell specific profile of a live cell in an aqueous medium and to then store this information in the memory storage element. In some embodiments of the invention, cells can be arrayed for more uniform, higher density, and higher throughput analysis (e.g. by photoresist deposition processes known in the art) with "holes" (e.g. nanowells or microwells) of an appropriate size.

Embodiments of the invention useful for identifying a characteristic of a test cell can be coupled to computer systems and databases. Methods for identifying a characteristic of a test cell generally involve determining a cell characteristic profile of the test cell to generate a test profile, and comparing the test profile with a reference profile in a subject database. Such methods further include the generation of a library of profiles (e.g. one grouped according to specific physiological conditions associated with various profiles such as cellular sensitivity or resistance to a therapeutic agent) as well as comparisons of a test profile to profiles in a library of profiles. Such comparisons can use software processes known in the art to provide the best match, e.g., to identify a reference profile that is substantially identical to the test profile. The reference profile can then be used to correlate one or more characteristics of the test cell.

The cell characteristic profiles can be compiled in a database, as described above, and the information in the database is used to compare the profile of a test cell to a reference profile in the database. The comparison can be made by trained personnel (e.g., a clinician, a technician, etc.), or can be made by a computer or other machine. The subject diagnostic assays are useful for identifying any type of abnormal cell, for example, diagnostic assays of the invention are useful for identifying cancerous cells in a biological sample, e.g., a biopsy, as well as in an individual in vivo.

The data obtained from analysis of various cell types under various physiological conditions and in various physiological states can be compiled in a database in order to, for example, train neural networks for independent detection of cell types and physiological status of cells. The cell characteristic profiles are obtained as described above, and the neural network is trained to recognize cells of various cell types, cells in various physiological states, and cells responding to various stimuli. The neural network is useful for identifying cancerous cells, pre-cancerous cells, and cells in other pathological conditions.

General methods and materials that can be adapted for use with embodiments of the invention are disclosed in U.S. Patent Application Nos. 20100284016, the contents of which are incorporated herein by reference. Further aspects, elements, and processes associated with embodiments of the invention are disclosed below.

As noted above, embodiments of the invention relate to Live Cell Interferometry techniques. Such techniques are known in the art. An illustrative and non-limiting list of publications that describe live cell interferometry (LCI) systems, methods, and materials are disclosed for example in Teitell et al., U.S. Patent App. Pub. No. 2010/0284016; Popescu et al., U.S. Patent App. Pub. No. 2009/0290156; Reed, J. et al., *ACS Nano*. 2008, 2, 841-6; Reed, J. et al. *Nanotechnology* 2008, 19, 235101; Reed, J. et al. *Biophys J.* 2011, 101, 1025-31, the contents of which are incorporated by reference.

Figure 2:
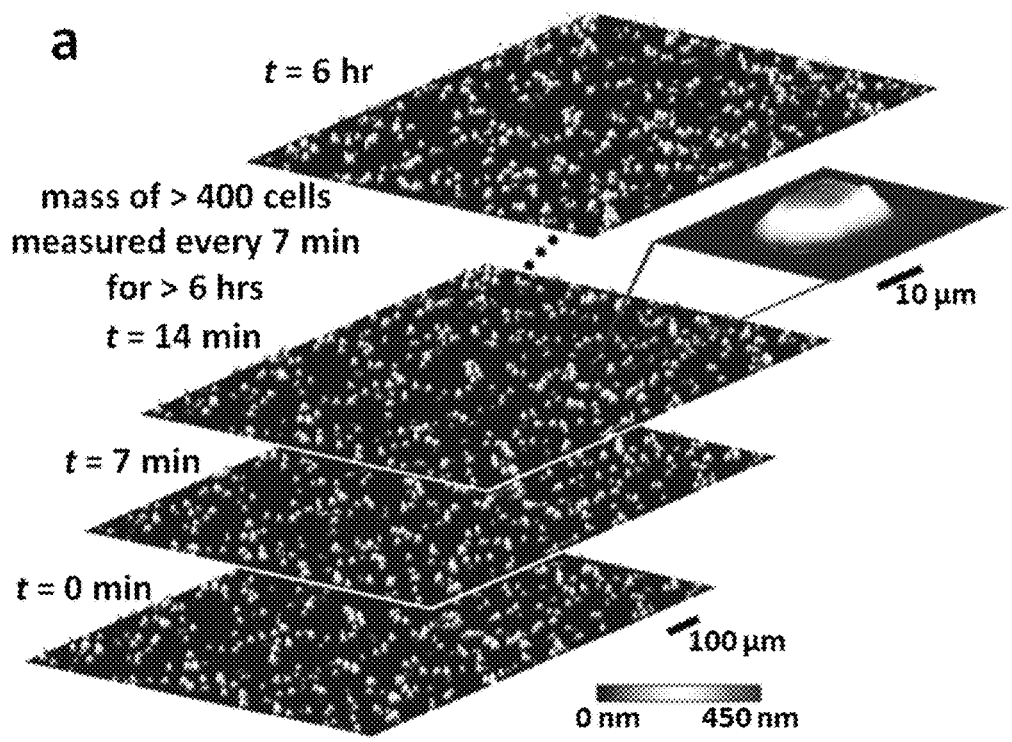
FIG. 2 illustrates high-throughput and longitudinal measurements of cell mass with LCI. Four sample images of H929 multiple myeloma cells (a) from the LCI show optical thickness profiles of cells over six hours of monitoring. Color indicates the phase shift in nm, with dark blue indicating low thickness and white/red indicating high thickness. These sample images are composites of 25 successive CCD captures taken every 7 minutes. The inset shows a measurement of the phase shift across a single cell. Integrated phase shift across a cell is directly proportional to cell dry mass. (b) Hundreds of individual cells (outlined in red) are identified at unique positions in each frame and (c) the mass of each individual cell is determined, enabling high-throughput, population-level mass profiling over time. (d) The mass of individual cells is tracked longitudinally over time to examine single cell growth dynamics. Measurements are shown as open symbols with a linear least squares best fit line. The measured growth rate in this case is 6.5 (se+/−0.72) pg/hr. The variation about the linear trend, taken as the standard deviation of the residual error, is 5.0 pg or 1.17% of the median cell mass. The maximum peak-to-peak residual error is 11 pg at 102 minutes or 2.61% of the median mass at that time point.
Figure 5:
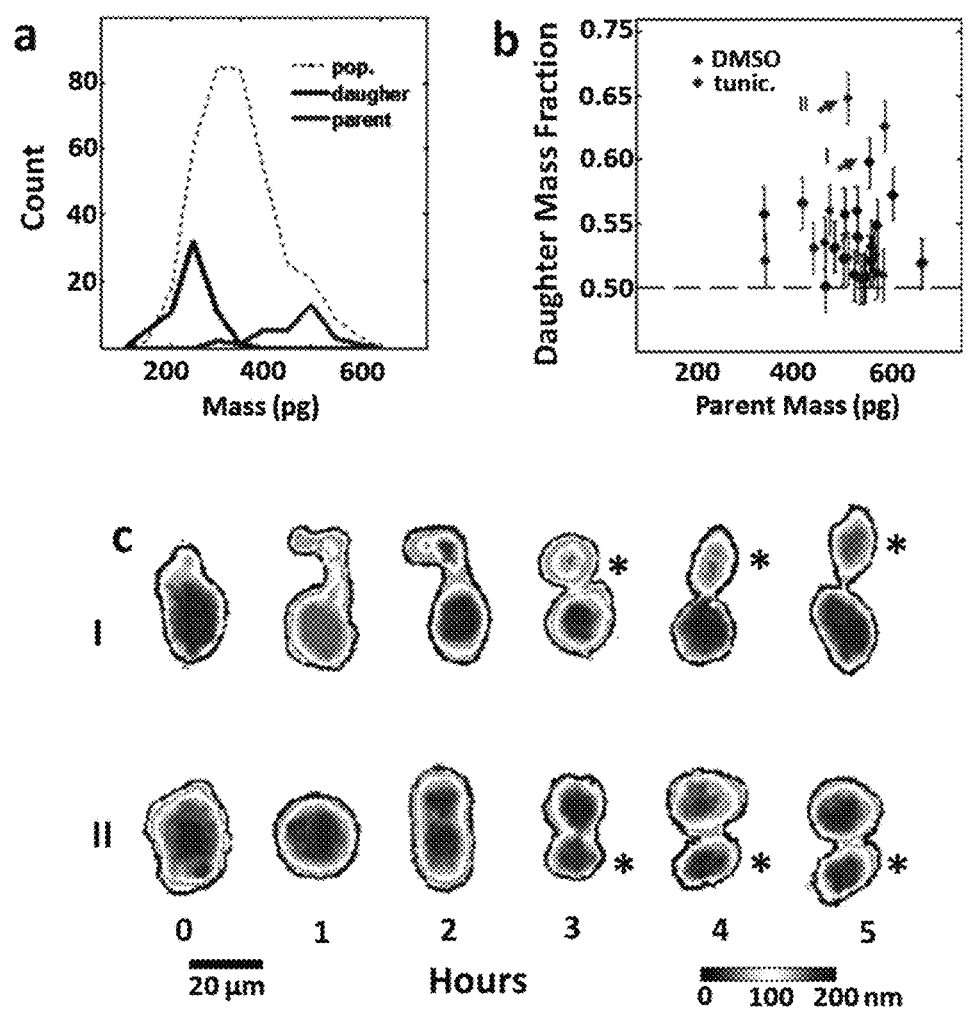
FIG. 5 illustrates mass dynamics of cell division. Twenty eight division events were recorded from the treated and untreated populations in all experiments (from a total of ~600 cells). (a) The mass range of dividing cells was determined by observing individual divisions and measuring the mass of the parent and daughter cells directly. Panel (a) compares the mass distribution of all cells measured (both treated and untreated; dashed line) with the masses of those cells which divided during the experiment (red before the division, blue after division). (b) Surprisingly, a number of cell divisions were highly asymmetric, with ~55%, or more, of the total parent cell mass remaining in the smaller of the two daughter cells. (c) Two examples of highly asymmetric division are shown over the five hour time course. The smaller of the daughter cells in these divisions (indicated by an asterisk) contained 35% and 40% respectively, of the parent cell mass. These division events are indicated by red-filled circles in (b). Error bars represent +/−2% CV, an estimate of the measurement error (see Methods).

The physical principal underlying LCI is as follows: The variation in phase imparted to coherent or semi-coherent light propagating through a transparent cell body is linearly proportional to the material density of the cell (9-11). Interference microscopy can measure these changes in phase, for micron-sized objects, to a precision exceeding $\frac{1}{1000}$ of a wavelength, or better than 0.5 nm for visible light. Cell mass can then be related to the measured phase retardation of each cell as: (9)

$$m = \frac{1}{\alpha} \int \varphi \lambda dA$$

Where m is the mass of the cell, $\alpha$ is a constant describing the relationship between phase shift and cell mass, $\varphi$ is the measured fractional phase shift, $\lambda$ is the illumination wavelength, and integration is performed across the entire cell area, A. Here, $\alpha=1.8\times10^{-3}$ m$^3$ kg$^{-1}$, consistent with Ross (9) as an average value taking into account the usual contents of a cell. The exact value of $\alpha$ is not known, however, based on prior, independent measurements, it is assumed that: (1) $\alpha$ remains constant across a wide range of concentrations and (2) $\alpha$ is not likely to vary more than approximately 5% due to changes in cellular content. (11-13) Nevertheless, the specific value of $\alpha$ will not affect the accuracy of measurements of comparative growth rates (c.f. FIG. 2, 3) and relative daughter cell masses after cell division (c.f. FIG. 5). FIG. 1 shows a schematic of the LCI, and typical optical thickness images of adherent and non-adherent cells.

Because it is a wide-field imaging technique, LCI provides simultaneous mass measurements of hundreds of cells (FIG. 2). Throughout the data collection, cells can be maintained in standard culture dishes in physiological conditions (e.g., pH 7.4, 37° C., 5% $CO_2$) enabling periodic, longitudinal measurements for 6 hours or longer (FIG. 2*a*). With an automated image processing algorithm, hundreds of cells can be identified and mass-profiled in each image in rapid succession (FIG. 2*b*). In these conditions, the single-cell mass measurements are highly repeatable (<3% CV; see Methods: Measurement Errors). At each time point, therefore, the population-wide distribution of cell mass can be determined (FIG. 2*c*). Furthermore, individual cells can be tracked over long times to yield growth rate curves (non-aqueous cell mass changes), as in FIG. 2*d*.

The following examples are provided so that the invention might be more fully understood. These examples are illustrative only and should not be construed as limiting the invention in any way.

Example 1: Illustrative Methods and Materials Useful with Embodiments of the Invention Interferometer The live cell interferometer has been described in detail previously (1). Briefly, the system is an optical microscope, based on a modified Veeco NT9300 optical profiler, with a 20×0.28NA Michelson interference objective that allows for the observation of not only lateral features with typical optical resolution (1.16 μm for the 20× objective) but also height dimensions of reflective objects below the scale of one nanometer. The Michelson interferometer is composed of a beam splitter, reference mirror and compensating fluid cell to adjust for optical path differences induced by fluid surrounding the specimen. The phase shifting interferometry (PSI) (14) method was used to capture phase images of the cell bodies in situ. During measurement, a piezoelectric translator decreases the light path a small amount causing a phase shift between the test and reference beams. The system records the irradiance of the resulting interference pattern at many different phase shifts and then converts the irradiance to phase wavefront data by integrating the irradiance data using a PSI algorithm. As currently implemented, the autofocus and PSI measurement cycle takes 12 seconds. The PSI measurement itself takes 1-2 seconds, and is limited by the camera frame rate (60 fps). In this experiment, one set of 25 images, containing 400-1,000 cells, was captured every 7 minutes. Each set of 25 images contained hundreds of cells, with data from the first five images presented here, and therefore each run includes ~80 cells. All cells within each of the selected images were measured.

Data Analysis

The software native to the Veeco NT9300 allows automated optical thickness measurements of cells selected manually from the phase image. The optical thickness is converted to mass as described in the text, using the conversion constant, $\alpha=1.8\times10^{-3}$ m$^3$ kg$^{-1}$, consistent with Ross. (9) The boundary of each cell was automatically selected by an algorithm that partitions objects from the background using a threshold determined from the histogram of pixel heights. (15) Conversion of the raw phase image into optical thickness uses a series of well established 'phase unwrapping' routines. (16) Occasionally, this conversion from phase to optical thickness is incorrect by a factor of negative one wavelength (530 nm), which causes contiguous regions with the cell to have an apparent optical thickness one wavelength less than the true value. This error is easily detected as a non-physical discontinuity in optical thickness, and corrected by adding back one wavelength of optical thickness to the affected pixels. This process is not fully automated at present.

Quantification of Measurement Errors

Figure 8:
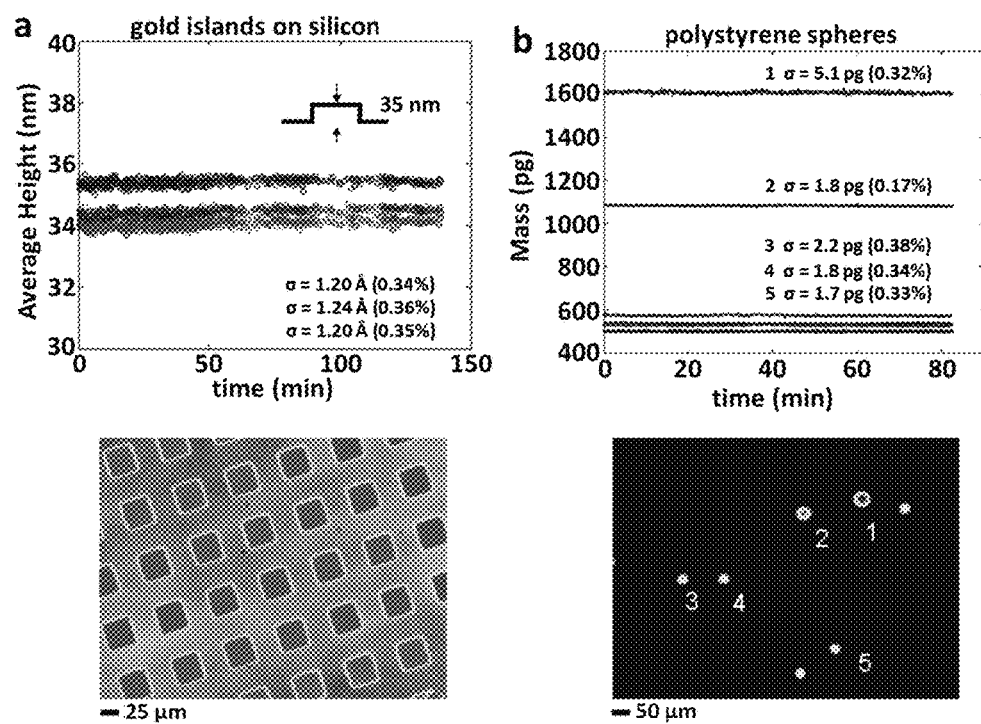
FIG. 8 illustrates the optical path and mass measurement stability of LCI. Gold islands vapor deposited onto silicon (a, lower panel), ~35 nm in height, were measured repeatedly for 140 minutes to test the stability of the interferometer. Shown in the top panel, the mean height of three representative islands shows no meaningful drift during this period and the measurement repeatability, given as the standard deviation of the height, is ~1.2 angstroms or 0.35% of the total height. Similarly, stability of the mass measurement for transparent objects is estimated by repeatedly measuring partially-melted 10 um diameter polystyrene spheres (b) over 80+ minutes. In the top panel, trace #1 represents three spheres melted into a cluster, and trace #2 represents two spheres melted into a cluster. The other three traces are from single spheres. The coefficient of variation of the mass measurement for the polystyrene spheres is similar to that obtained for the mean height of the gold islands, <0.4%, with negligible drift over the measurement period. Data were collected in the LCI observation chamber under conditions identical to those used to measure live cells, with the exception that water replaced the culture medium.
Figure 9:
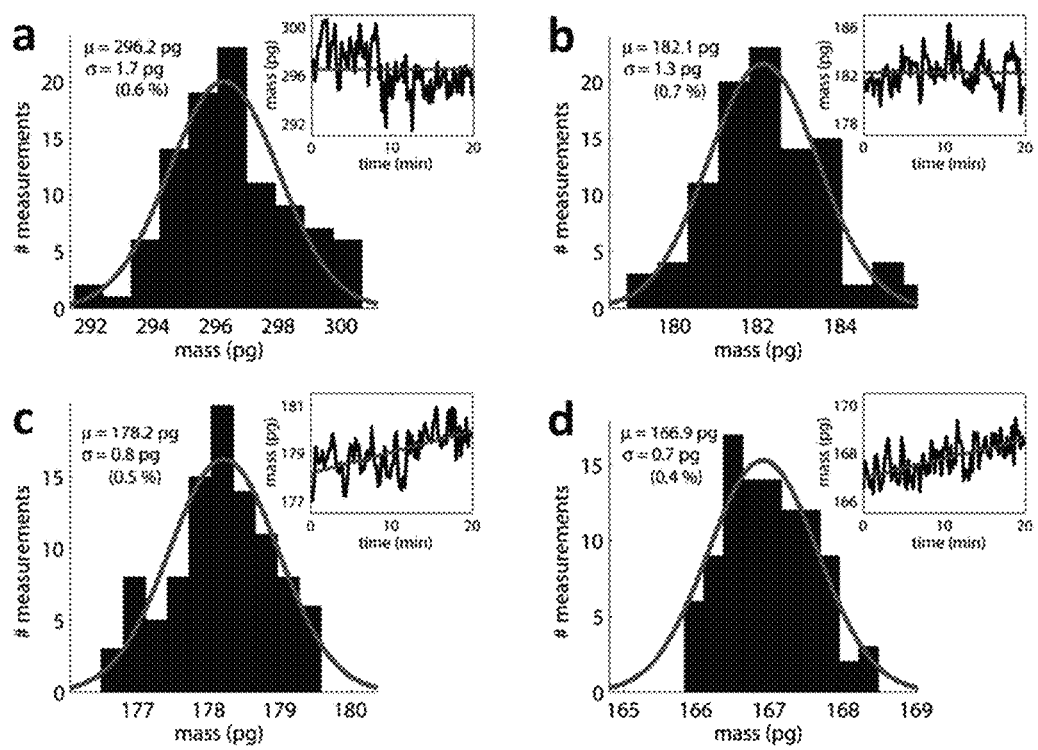
FIG. 9 illustrates high precision mass measurements with LCI. Four individual cells (a through d) were selected and tracked over 98 successive measurements made at roughly 12 s intervals. Over this time period (20 min total) the observed cells showed small changes in mass (see inset plots of mass vs. time), allowing assessment of measurement repeatability. Cells in c and d show >one picogram average mass change over this period, so histograms in c and d present measured mass minus the linear component of the least-squares fit line (shown in red in the inset) to remove any additional variance due to growth. Histograms of measurements for each cell were fitted to a Gaussian distribution by nonlinear least-squares fitting in Matlab. Mean ($\mu$) and standard deviation ($\sigma$) are reported for each distribution. All standard deviations are <1% of the distribution mean indicating that mass measurements with the LCI are highly repeatable.
Figure 10:
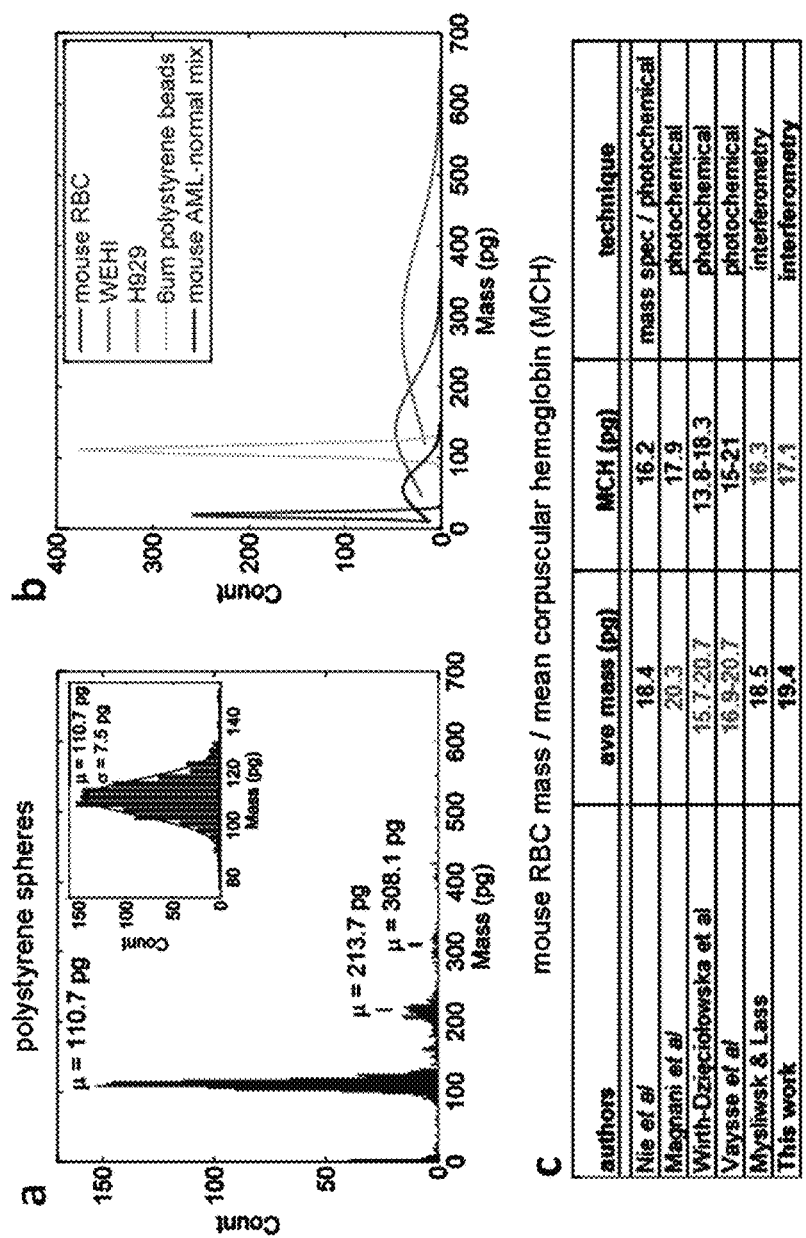
FIG. 10 illustrates the mass of a population of partially melted 6 μm diameter polystyrene spheres (Flow Check, Polysciences Inc.) that were measured by LCI in water (a). During preparation the spheres infrequently aggregate and upon heating dimers and trimers coalesce into single, conical clusters. Peaks for the population of monomers (110.7 pg), dimers (213.7 pg) and trimers (308.1 pg) can be distinguished in the histogram. The LCI-measured standard deviation of the monomer population mass is 7.5 pg, or 6.8% of the mean, which exceeds the manufacturers' stated specification of 15%. The mass distribution of populations of four different mammalian cells types and the 6 um polystyrene spheres are plotted together as histograms for comparison (b). The mean mass of the mouse red blood cell (RBC) population determined with LCI can be compared to published values determined by other techniques (see, e.g. Nie, Z., et al. *Analytical Chemistry*, 2007. 79: p. 7401-7407; Vaysse, J., et al. *Mechanisms of Ageing and Development*, 1988. 44(3): p. 265-276; Wirth-Dzieciolowska, E., et al. *Animal Science Papers and Reports*, 2009. 27(1): p. 69-77; Magnani, M., et al. *Mechanisms of Ageing and Development*, 1988. 42(1): p. 37-47), and by another group using microinterferometry (see, e.g. Mysliwski, A., et al. *Mechanisms of Ageing and Development*, 1985. 29(2): p. 107-110) (c). Nie et al measured the cell mass of mouse RBCs using a novel mass spectrometric method, and also the mean corpuscular hemoglobin mass (MCH) by traditional photochemical techniques (see, e.g. Nie, Z., et al. *Analytical Chemistry*, 2007. 79: p. 7401-7407). The MCH typically represents a large fraction of the total cell mass of mammalian red blood cells. The range of MCH values for various mouse strains are well established (see, e.g. Magnani, M., et al. *Mechanisms of Ageing and Development*, 1988. 42(1): p. 37-47; Mysliwski, A. et al. *Mechanisms of Ageing and Development*, 1985. 29(2): p. 107-110; Wirth-Dzieciolowska, E., et al. *Animal Science Papers and Reports*, 2009. 27(1): p. 69-77). Using the ratio of MCH-to-total mass given by Nie et al. as an estimate, the established values for mouse RBC MCH can be compared to the average mouse RBC mass measured. The estimated values are displayed in red.
Figures 1, 11:
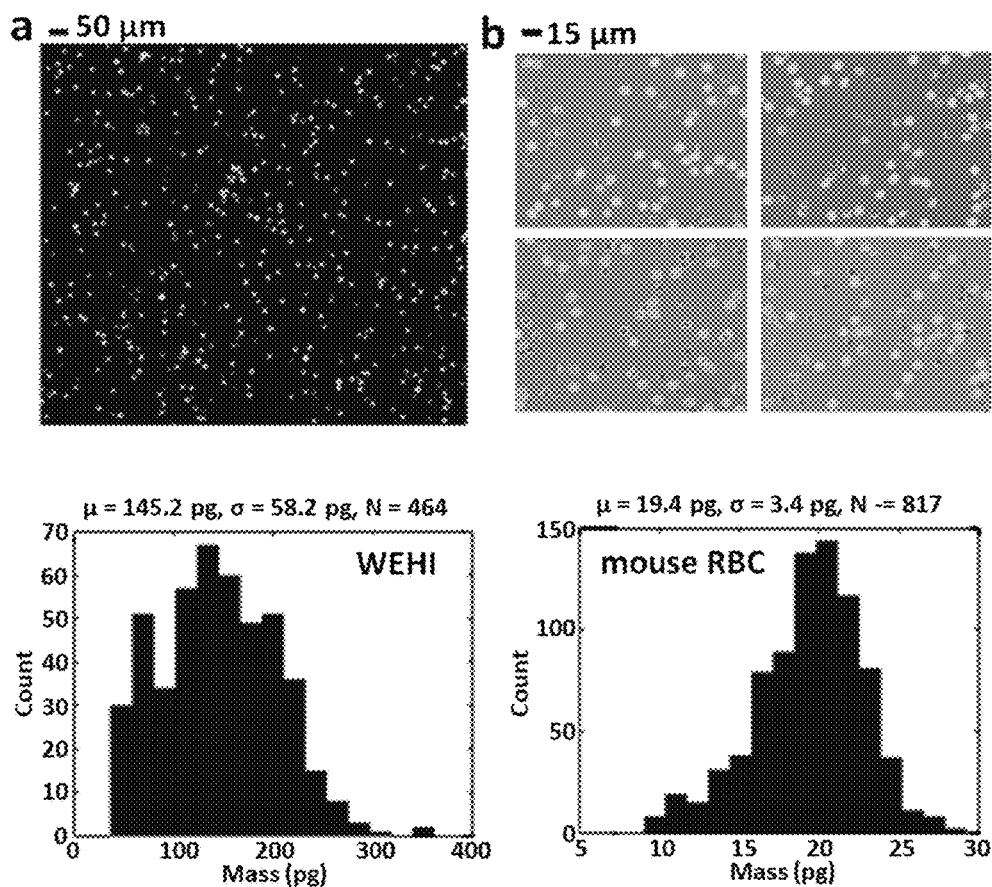
FIG. 11 illustrates the mass distributions of populations of four different live or freshly prepared cell types were measured by LCI: (a) mouse WEHI-231 B lymphoma cells (b) red blood cells (RBCs) from a 15 week-old female C57BL/6 mouse, (c) human H929 multiple myeloma cells, and (d) a mixture of primary bone marrow and acute myeloid leukemia (AML) cells established in a C57BL/6 mouse by retroviral transduction and adoptive cell transfer using standard techniques.
Figures 2, 11:
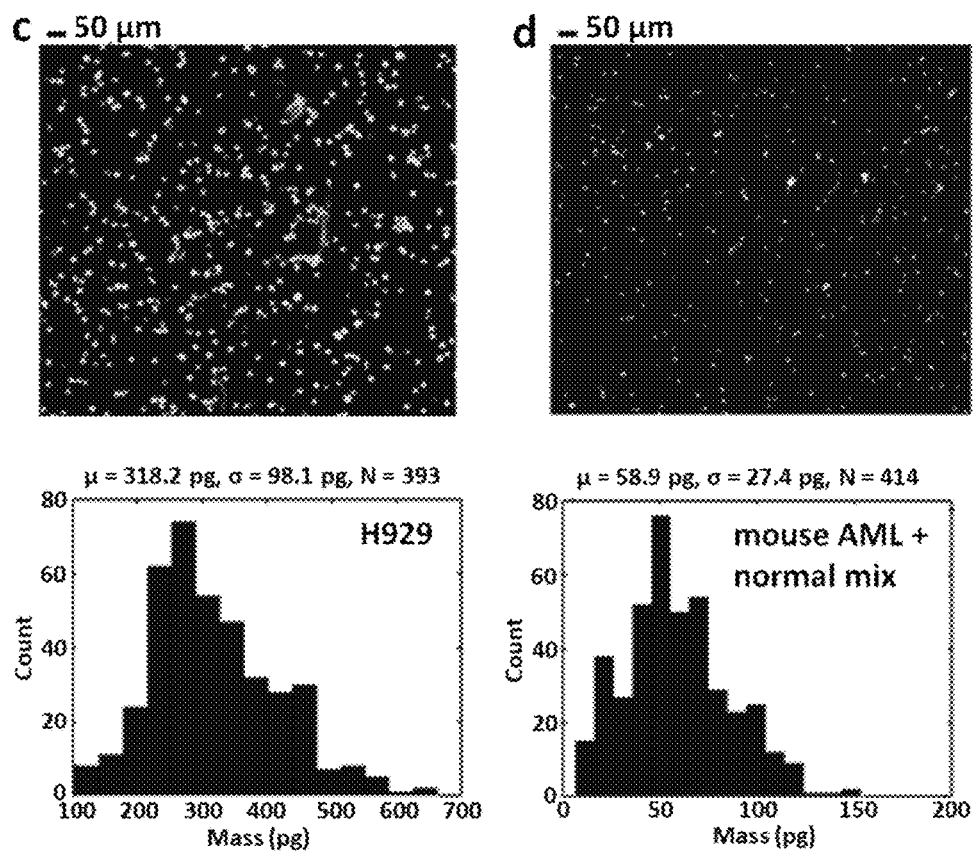
Figure 12:
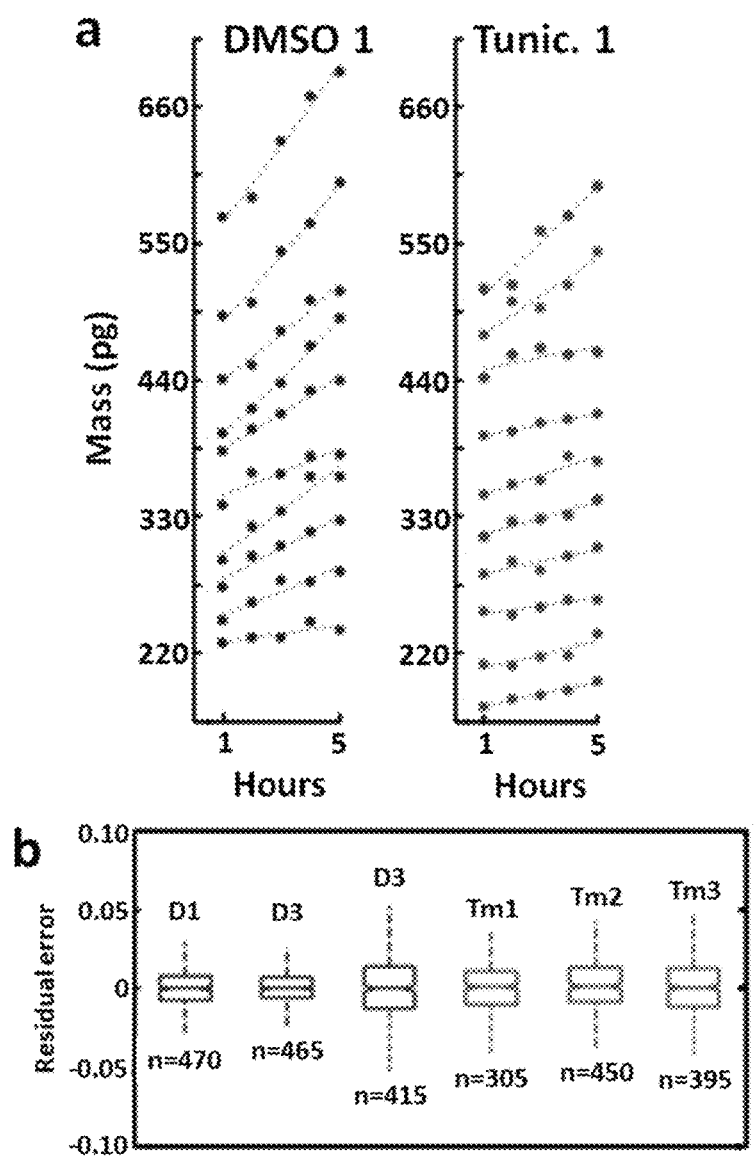
FIG. 12 illustrates mass vs. time plots (a) for representative cells from the data given in FIG. 9a. The dashed lines represent an exponential growth fit to the data. To estimate the scale of measurement variation in the live cell experiments, all single-cell mass vs. time data, from all three Tm-treated and DMSO control runs (indicated D1-D3 and Tm1-Tm3, respectively), were fitted to a simple exponential growth model (mass(t)=$m_0 * C^t$, where the constant C is close to unity), and residual error calculated as the percent difference between the trend and the actual data at each time point. In the box plot, the central line indicates the sample median, and triangles indicate the 95% confidence interval for the median. Solid boxes indicate limits of the 25 and 75 percentiles, and whiskers represent two standard deviations from the mean. The residuals are symmetrically distributed about zero, and the range between the 25% and 75% quartile (IQR) varies from 0.0126 (D2) to 0.027 (D3). The mean IQR is 0.02.

The accuracy of interference microscopy for cell mass measurements is firmly established in electromagnetic theory, (17, 18) and by a variety of reference techniques that include ultracentrifugation, (3, 4, 10-12, 19-21) refractometry of protein solutions, hydrogels and transparent films, (22-24) x-ray densitometry, (25) and electron microcopy. (26-30) To characterize the accuracy and stability of the LCI system, we conducted several benchmark experiments, the detail for which is given in FIGS. 8-11. The lower limit of coefficient of variation (CV) for LCI mass measurements, which is a function of the temporal stability of the interferometric optical path (1.2 angstroms; FIG. 8*a*) was determined to be ~0.35%. Similar CVs were determined for serial measurements of partially melted polystyrene beads, which simulated cells (CV<0.4%; FIG. 8*b*), and for short repeated measurements of actual live cells (CV<1%; FIG. 9). We measured populations of 6 μm diameter polystyrene spheres (FIG. 10*a*) normally used as calibration standards in flow cytometry (Flow Check, Polysciences Inc), and for which a population mean volume and standard deviation are provided by the manufacturer; the population mass CV determined by LCI (6.8%) was considerably smaller than that determined by the manufacturer (15%). We also measured a population of red blood cells (RBCs) freshly obtained from a 15 week old female C57BL/6 mouse (FIG. 10*b*-*c*). Mouse RBCs serve as an informative independent standard because there exits an established range of values for average cell mass (determined by photochemical and other methods). Our LCI-determined value of mean RBC cell mass, 19.4 pg, is in excellent agreement with the range of published values at 15-21 pg. (9-12, 31) Finally, for comparison we measured the masses of populations of a variety of mammalian cell types (FIGS. 10b, 11). These are plotted together with the mouse RBC and polystyrene sphere data in FIG. 9b. To estimate the scale of measurement variation in multi-hour live cell experiments, all single-cell mass vs. time data, (representing ~480 cells) were fitted to a simple exponential growth model (mass(t)=$m_0*C^t$, where the constant C is close to unity) and residual error calculated as the percent difference between the trend and the actual data at each time point (FIG. 12a). The residuals are symmetrically distributed about zero (FIG. 12b) and the range between the 25% and 75% quartile (IQR) varies from 0.0126 (c2) to 0.027 (c3). The mean IQR was 0.02. Taken together, these results indicate a lower bound of measurement repeatability on the order of 0.5-1.0% and an outer bound of 2.0-3.0%. The main difference between short- and long-term measurements of live cells is the shape change which occurs over the scale of hours. This can cause added variation in the integrated optical thickness from: (1) small errors in partitioning the cell boundaries, (2) optical 'averaging' of closely spaced fringes present at the edge of 'rounded' cells, and (3) a potential change in the value of a, the mass-to-optical thickness constant, although previous work suggests this error would be relatively small. (3) It is established that (1) α is unaffected by changes in concentration, even up to the limit of crystallized protein solutions (9), (2) α reflects the mass interacting with light at a specific location (9-12, 31) and is, therefore, not affected by how much area the cell occupies within the field of view as it grows, and (3) the value of α remains close to 0.0018 over a wide range of materials found in cells. (32)

Cell Lines and Tissue Culture

H929 human multiple myeloma cells were maintained at 37° C. in 5% $CO_2$ in RPMI 1640 growth media supplemented with 10% defined fetal bovine serum (HyClone) and antibiotics. The observation chamber was 4.5 cm in diameter and 1.5 cm deep with a 2×2 cm silicon substrate placed on top of a plastic shelf such that the silicon was near the top of the fluid surface. The imaging cell was completed by a piece of optical glass (BK7 glass, Quartz Plus, Inc., Brookline, N.H.) separated from the silicon surface by resting on top of three 600 μm stainless steel beads (Salem Specialty Ball Company, Canton, Conn.) to create a uniform thickness sample chamber. Media bubbled with 5% $CO_2$ air was continuously flowed through the incubation chamber using a peristaltic perfusion pump at a rate of 0.5 mL/min. The 530 nm wavelength LED illumination (Luxeon Star LED, Brantford, Ontario) incident on the sample chamber had a power of 15 μW spread over a 1.2 mm diameter illumination spot. Cell responses to external stimuli were measured for as long as seven hours in this configuration, and observed unperturbed cultures for up to twelve hours, although the upper limit of experiment duration has not been determined.

Drug Treatment, Cell Cycle Analysis, and Nucleic Acid Isolation

H929 cells were seeded in 6-well culture plates at a density of 1×$10^6$ cells/well. Before plating cells in the LCI's observation chamber, either 1 μL of Tunicamycin (T7765; Sigma-Aldrich) in DMSO, or DMSO alone were added to the media at a concentration of 10 mg/ml, DMSO/media (1:1000 dilution). Mass measurements commenced one hour after the cells were plated in the observation chamber in order to allow the experimental system to stabilize, i.e.; culture acclimation, temperature stabilization, etc. For cell cycle analysis, cells from each time point were collected and incubated with a hypotonic DNA-staining buffer containing propidium iodide and later analyzed by flow cytometry. RNA for each time point was extracted using the Trizol reagent (Invitrogen).

Reverse Transcription, RT-PCR, and Quantitative RT-PCR

CDNA was synthesized from 3 μg of total RNA with oligo(dT) primers using the Superscript III first strand cDNA synthesis kit (Invitrogen). RT-PCR for XBP1 spliced and unspliced isoforms were performed using Platinum Taq (Invitrogen) at an annealing temperature of 58° C. for 25 cycles. Quantitative RT-PCR for CHOP (DDIT3) mRNA was performed using the SYBR green real time PCR kit (Diagenode) and an Applied Biosystems (Foster City, Calif., USA) 7700 sequence detector as described (33). Samples were analyzed for 36b4 expression as a normalization control. Primer sequences are available on request.

Results and Discussion

Mass accumulation dynamics have not been previously reported on a cell-by-cell basis over long time scales (several hours) for an entire population of ~100 cells measured simultaneously. To test the hypothesis that LCI mass profiling can rapidly determine a response to external cell stimuli, such as a drug response, we exposed H929 multiple myeloma cells to the drug tunicamycin (TM), a protein glycosylation inhibitor, (34) and compared the growth profiles of TM-treated to untreated control cells by measuring mass continuously over five hours.

Figure 3:
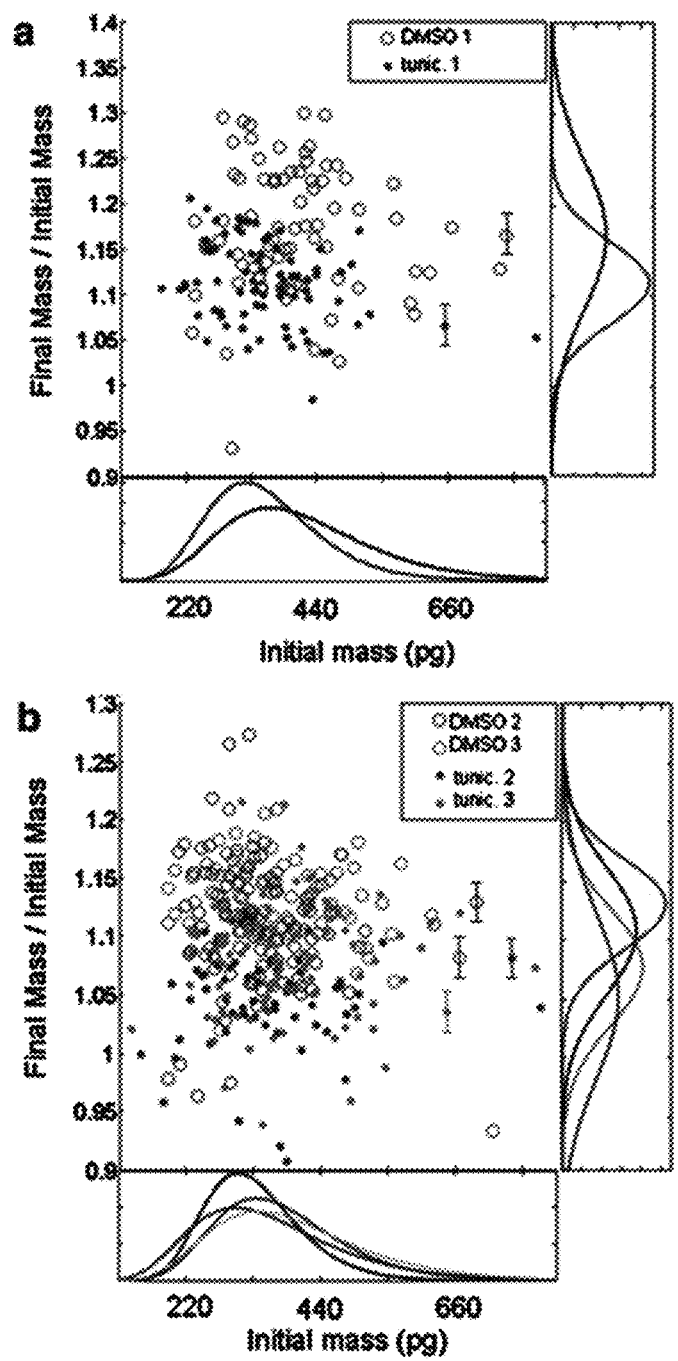
FIG. 3 illustrates a drug response of H929 multiple myeloma cells as profiled by single-cell mass accumulation. Results of LCI longitudinal mass measurements on populations of H929 multiple myeloma cells, comparing the mass accumulation of DMSO-treated controls with Tunicamycin-treated (10 g/ml) cells. Data are taken over five hours. The treated cells grow more slowly than do the controls. Experiments #2 and #3 were conducted at 32° C., versus 37° C. for #1, which accounts for the slightly lower overall growth rates observed. The scatter plots (a-b) depict the growth of individual cells at five hours versus their initial mass (normalized by initial mass). Error bars represent +/−2% CV, an estimate of the measurement error. Error bars apply to all data, but are omitted for the majority of points in the plot for clarity. In the box plots of normalized mass versus time (c-d), circles indicate the sample median, and triangles indicate the 95% confidence interval for the median. Solid boxes indicate limits of the 25 and 75 percentiles, and whiskers represent two standard deviations from the mean.

We determined that the initial distribution of H929 cell masses is approximately log normal, with a range of 200 to 700 pg. The majority of cells had mass>200 pg and <400 pg, while a small fraction (36%) are much larger than average, with masses above 500 pg. Both the treated and untreated populations exhibited growth, but the mass accumulation rate was much lower in the treated cells (FIG. 3). The growth profiles of both populations are clearly heterogeneous (FIG. 3a-b), and in both, a minority of cells exhibited either a vigorous increase in mass (+15% growth), or little to no mass accumulation (<5% growth). The suppression of growth of the treated population appears within two hours, and is readily apparent by the fourth hour (FIG. 3 c-d). Thus, whole population detection and quantification of cell drug responses were attained within several hours of treatment. The variation in growth rates within the treated and untreated groups (FIG. 3 c-d) at five hours approached the magnitude of the variation between treated and untreated cultures at the same time point. These experiments were conducted on separate days, with distinct subcultures taken from a master stock. Therefore, they are 'biological' not 'technical' replicates, and the difference in behavior likely reflects biological variation. We used technical replicates on controlled samples to estimate the measurement error to be <3% CV. Nonetheless, we note that the differences in normalized final mass (final/initial) between each treated sample and each untreated sample are statistically significant with p<0.05 (FIG. 3 c-d). This provides evidence that the LCI is capable of detecting differences in growth rates between treated and untreated populations of cells.

Figure 7A:
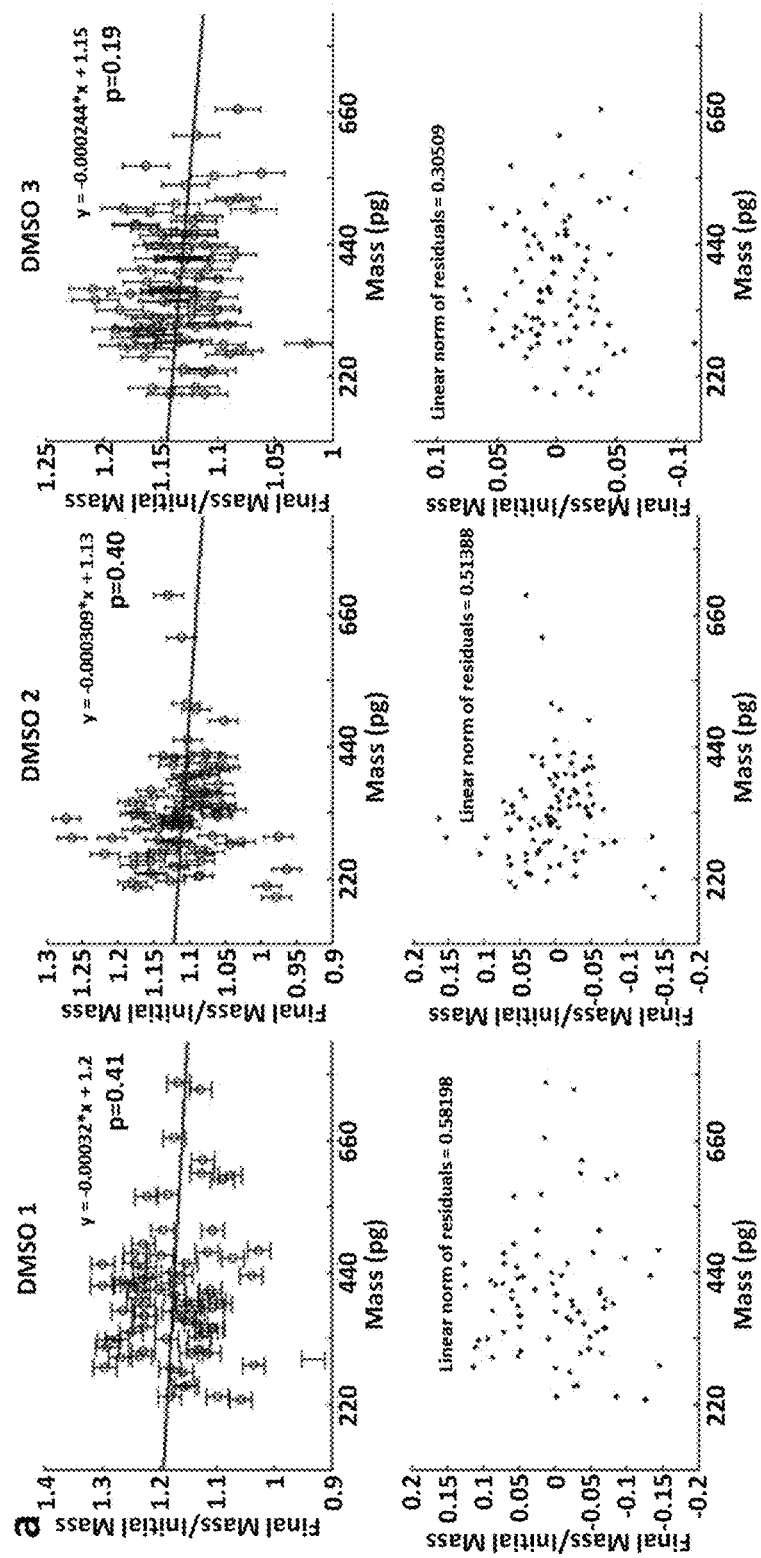
FIG. 7 illustrates scatter plots of treated and untreated data sets. The red trend line represents a linear least-squares fit to the data. The p value, indicating the probability that there is no correlation between growth rate and cell mass, is given for each fit. There is a trend toward a slower growth as cell mass increases in the untreated controls, although this is not statistically significant to 95% confidence. The treated sets Tm2 and Tm3 show no correlation between growth rate and mass, while the negative slope is significant (p=0.02) for Tm1. The norm of the residuals for each linear fit provides an estimate of growth variation within each mass segment. Error bars represent +/−2% CV, an estimate of the measurement error.
Figure 7B:
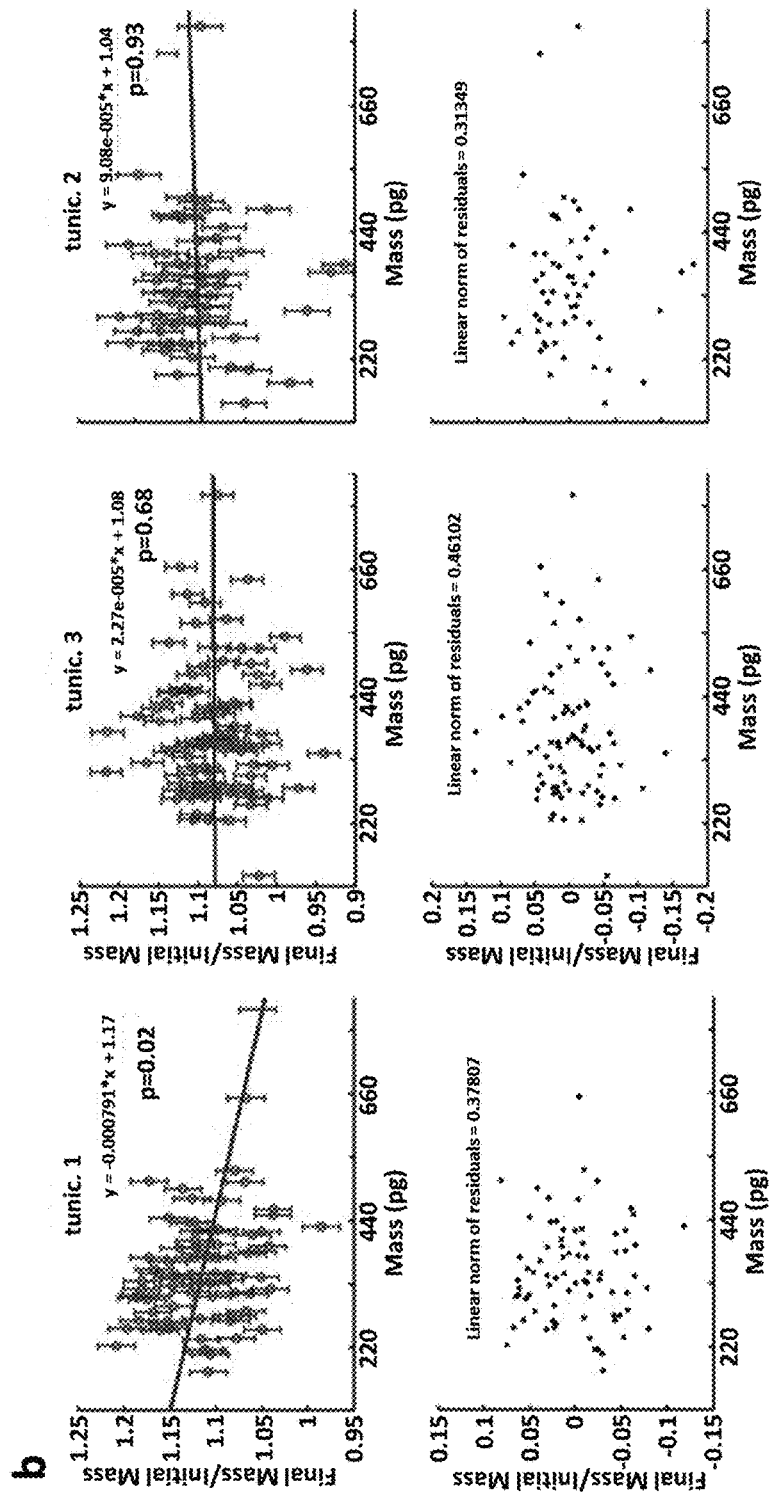

At the single cell level, the growth rate of individual cells is largely independent of cell mass, within experimental error, for both treated and untreated cells (FIG. 7). An exception is treated population Tm1, which showed a statistically significant linear trend toward slower growth in its larger cell subpopulation. The reason for this difference is unclear. Interestingly, the spread in growth rates within any particular mass fraction cannot be explained entirely by measurement error, suggesting a biological origin of this variation as well. This variation, taken as the norm of the residuals of a linear least squares fit to the growth versus mass data, ranges from 3.15.8% (FIG. 12), while we estimate mass measurement error is <3% CV (see discussion of errors in Methods).

Figure 4:
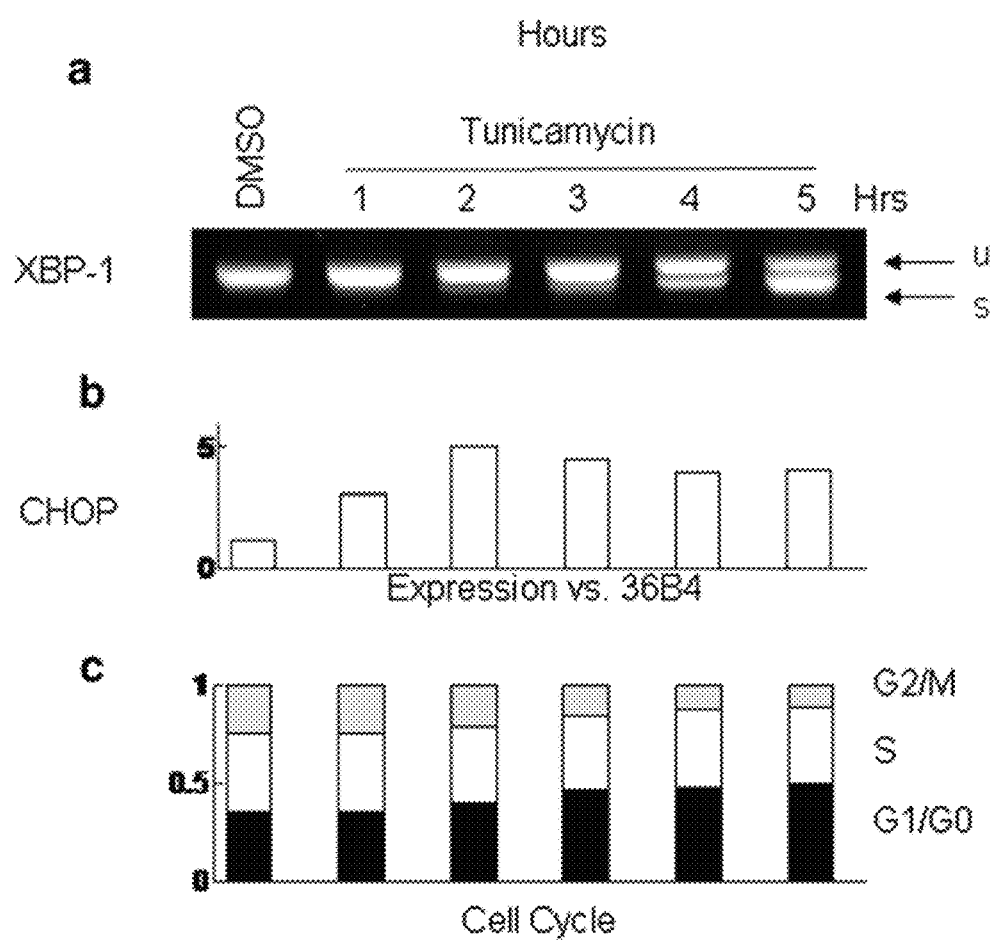
FIG. 4 illustrates a molecular profile of H929 response to Tunicamycin. The divergence in growth rates between the treated and untreated populations occurs synchronously with the up-regulation of the transcription factor CHOP (a) and the alternative splicing of transcription factor XBP1 (b) in the treated population. CHOP and XBP1-s activate a host of genes responsible for mitigating the effects of protein misfolding in the endoplasmic reticulum. This is consistent with the known mechanism of TM action, an inhibitor of protein glycosylation. (c) Cell cycle data show a rapid reduction in the G2/M phase population and a corresponding increase in the G1/G0 population, consistent with cell cycle arrest. This shift becomes pronounced after three hours of treatment, leaving 50% of cells in G1/G0 by the end of five hours of treatment.

To link the kinetics of mass accumulation with biochemical signaling, we profiled molecular markers with PCR and conducted a cell cycle analysis on the treated population. The divergence in growth rates between the treated and untreated populations occurs synchronously with the up-regulation of transcription factors CHOP and the spliced form of XBP1 ('XBP1-s'), in the treated population (FIG. 4 a-b). CHOP and XBP1-s activate a host of genes responsible for mitigating the effects of protein mis-folding in the endoplasmic reticulum, through increased production of molecular chaperones to aid protein folding, and accelerated degradation of mis-folded proteins (the so-called unfolded protein response, UPR, and the ER-associated protein degradation, ERAD, pathway (35). This is consistent with the known mechanism of TM action. (34) Both the UPR and ERAD molecular pathways are emerging targets for therapeutic intervention in a wide range of diseases, including multiple myeloma.

XBP1 is a context dependent positive or negative regulator of cell growth and differentiation in multiple myeloma cells. (34) The molecular dynamics of its bipolar transcriptional potential is not well understood. In the context of our experiments, induction of XBP1 mRNA splicing is associated with slowing mass accumulation, but not cell shrinkage or apoptosis. This time-resolved, non-destructive measurement of cell mass greatly helps interpretations of conflicting pro- and anti-proliferate molecular signals, assayed through traditional techniques, including immunohistochemistry or qPCR. Cell cycle data show a rapid reduction in the G2/M phase population and a corresponding increase in the G1/G0 population, consistent with cell cycle arrest (FIG. 4 c). This shift becomes pronounced after three hours of TM exposure, leaving 50% of the cells in G1/G0 by the end of five hours of treatment. This is also consistent with observations that activation of the UPR pathway leads to cell cycle arrest. (35, 36)

We determined the mass range of dividing cells by observing individual divisions and measuring the mass of the parent and daughter cells directly. Twenty eight cell divisions were observed across all experiments, out of a total of ~600 cells. The number of divisions was skewed in favor of the untreated population 18:11. This is consistent with the observed higher growth rates in that population. The mass at which a cell divides was tightly regulated, and similar in both treated and untreated populations (FIG. 5a). The median mass at division was 515 pg (+/−75 pg), with the two resulting daughter cells each having a median mass of 250 pg (+/−40 pg). This results enable us to infer via mass values which individual cells in the population are likely to be in early-, mid- and late-phases of the cell cycle. While the mass fraction for the daughter cells was ~50/50 in most instances, a minority of cell divisions were highly asymmetric, with the smaller of the two daughter cells retaining less than 45% of the parent's cell mass (FIG. 5 b). Mass maps of two cells undergoing asymmetric cell division are shown in FIG. 5 c.

Figure 6:
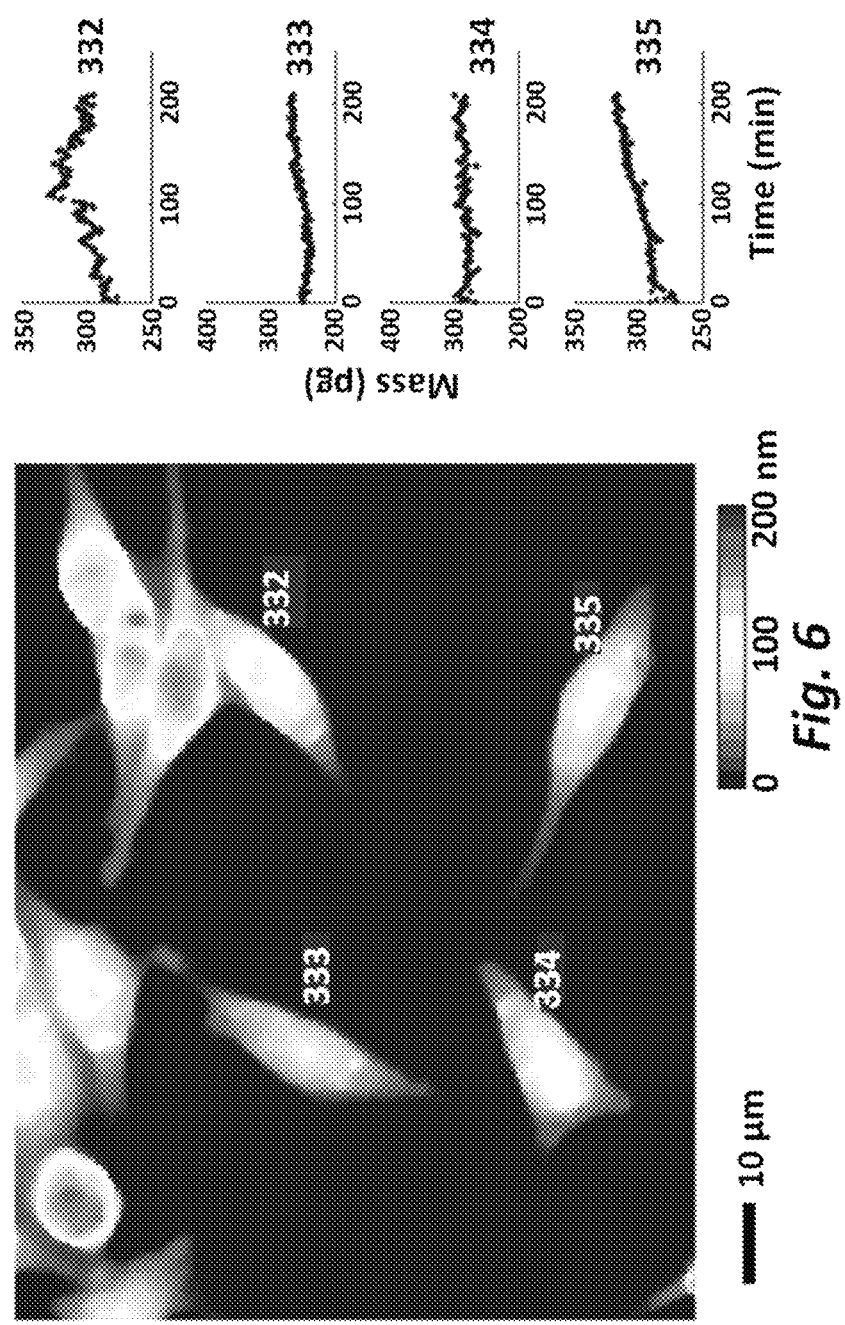
FIG. 6 illustrates live cell interferometer measurements of the mass of adherent cells. The frame shows several mouse fibroblast cells cultured directly on a polished silicon substrate. The color map indicates optical thickness measurements with blue being a low optical thickness relative to background and red being a high optical thickness. To the left are mass measurements of the four cells, as indicated, taken every two seconds for 200 minutes. The smaller optical thickness of the adherent cells vs. non-adherent cells is easily measured by the LCI.

There are clear advantages of LCI over other established and emerging methods for single-cell mass measurements. Unlike hollow cantilever MEMS mass measurement devices, (5, 6) which require non-adherent cells, LCI is equally compatible with adherent or non-adherent cells (FIG. 6). The ability to work with adherent cells is absolutely critical for probing the relationship between mass accumulation/distribution and cell:substrate interactions, and for assessing epithelial or stromal cell types, which form the bulk of human malignancies. LCI is also an excellent approach for linking mass profiling with a whole class of cell migration, motility, and tissue invasiveness assays commonly used in drug discovery. The interferometric microscope permits full optical access to the specimen, meaning high resolution light micrographs and fluorescent images are easily obtained. This enables the combined use of mass profiling and the extensive armamentarium of fluorescent reporter assays used in cell biology, for simultaneous assessments. Furthermore, LCI demonstrates quantification tracking and quantification of individual cell masses throughout, and following, cell division. This will directly enable, for the first time, broad spectrum profiling of mass partitioning in stem cells, for example.

LCI is high-throughput and allows longitudinal measurements of the same cells over time; it is also massively parallel, enabling hundreds of longitudinal measurements simultaneously and reducing inter-experiment error due to varying conditions. However, occasionally the conversion from phase to optical thickness is incorrect by a factor of negative one wavelength (530 nm), due to the ambiguity in phase shifts greater than $2\pi$. This situation causes contiguous regions with the cell to have an apparent optical thickness one wavelength less than the true value. This error is easily detected as a nonphysical discontinuity in optical thickness, and corrected by adding back one wavelength of optical thickness to the affected pixels. This correction process is not fully automated at present, although a substantial body of work addressing this issue exists in the literature (16).

We have measured cell responses to external stimuli for as long as seven hours, and observed unperturbed cultures up to twelve hours. In principle, measurements can continue for much longer durations since the cells remain viable for days under tightly controlled culture conditions. One limitation, common to LCI and alternative approaches (5, 7, 8), is the time required for the system to stabilize after cells are introduced into the observation chamber, or after media with a different temperature or density is introduced. In the present experiments, we have conservatively allowed one hour of settling time, although if required this settling time could be reduced by at least a factor of two.

In summary, high throughput LCI mass profiling is a sensitive and precise mechanism for quantifying single-cell, population based responses to environmental perturbations, such as medically-relevant drug responses.

A variety of methods and materials known in the art can be adapted to make and/or use embodiments of the invention, for example those disclosed in the following references:

REFERENCES IDENTIFIED IN ABOVE TEXT IN PARENTHESIS (1) Reed, J., M. Frank, J. J. Troke, J. Schmit, S. Han, M. A. Teitell, and J. K. Gimzewski, *High throughput cell nanomechanics with mechanical imaging interferometry*. Nanotechnology, 2008. 19(23).

(2) Reed, J., J. J. Troke, J. Schmit, S. Han, M. A. Teitell, and J. K. Gimzewski, *Live cell interferometry reveals cellular dynamism during force propagation*. ACS Nano, 2008. 2(5): p. 841-846.

(3) Barer, R. and S. Joseph, *Refractometry of Living Cells. 1. Basic Principles*. Quarterly Journal of Microscopical Science, 1954. 95(4): p. 399-423.

(4) Davies, H. G., M. H. F. Wilkins, J. Chayen, and L. F. Lacour, *The Use of the*

Interference Microscope to Determine Dry Mass in Living Cells and as a Quantitative Cytochemical Method. Quarterly Journal of Microscopical Science, 1954. 95(3): p. 271-&

(5) Godin, M., F. F. Delgado, S. M. Son, W. H. Grover, A. K. Bryan, A. Tzur, P. Jorgensen, K. Payer, A. D. Grossman, M. W. Kirschner, and S. R. Manalis, *Using buoyant mass to measure the growth of single cells*. Nature Methods, 2010. 7(5): p. 387-U70.

(6) Bryan, A. K., A. Goranov, A. Amon, and S. R. Manalis, *Measurement of mass, density, and volume during the cell cycle of yeast*. Proceedings of the National Academy of Sciences of the United States of America, 2010. 107(3): p. 999-1004.

(7) Park, Y. K., M. DiezSilva, G. Popescu, G. Lykotrafitis, W. S. Choi, M. S. Feld, and S. Suresh, *Refractive index maps and membrane dynamics of human red blood cells parasitized by Plasmodium falciparum*. Proceedings of the National Academy of Sciences of the United States of America, 2008. 105(37): p. 13730-13735.

(8) Popescu, G., Y. Park, N. Lue, C. BestPopescu, L. Deflores, R. R. Dasari, M. S. Feld, and K. Badizadegan, *Optical imaging of cell mass and growth dynamics*. American Journal of PhysiologyCell Physiology, 2008. 295(2): p. C538-C544.

(9) Ross, K. F. A., *Phase Contrast and Interference Microscopy of Cell Biologists*. 1967, London: Edward Arnold Ltd.

(10) Barer, R., *Interference Microscopy and Mass Determination*. Nature, 1952. 169(4296): p. 366-367.

(11) Davies, H. G. and M. H. F. Wilkins, *Interference Microscopy and Mass Determination*. Nature, 1952. 169 (4300): p. 541-541.

(12) Barer, R., K. F. A. Ross, and S. Tkaczyk, *Refractometry of Living Cells*. Nature, 1953. 171(4356): p. 720-724.

(13) Ross, K. F. A., *Phase Contrast and Interference Microscopy for Cell Biologists*. 1967: Edward Arnold Ltd.

(14) Schmit, J. and K. Creath, *Window function influence on phase error in phase-shifting algorithms*. Applied Optics, 1996. 35(28): p. 5642-5649.

(15) Otsu, N., *A Threshold Selection Method from Gray-Level Histograms*. IEEE Transactions on Systems, Man, and Cybernetics, 1979. 9(1): p. 62-66.

(16) Ghiglia, D. and M. Pritt, *Two-Dimensional Phase Unwrapping: Theory, Algorithms, and Software*. 1998: John Wiley & Sons.

(17) Adair, G. S., A. G. Ogston, and J. P. Johnston, *Osmotic Pressures and Sedimentation Velocity of Gastrophilus Methaemoglobin*. Biochemical Journal, 1946. 40(56): p. 867-869. (18) Pedersen, K. O., *Ultracentrifugal and electrophoretic studies on the milk proteins. II. The lactoglobulin of Palmer*. Biochemical Journal, 1936. 30: p. 961-970.

(19) Adair, G. S. and M. E. Robinson, *The specific refraction increments of serum-albumin and serum-globulin*. Biochemical Journal, 1930. 24(4): p. 993-1011.

(20) Davies, H. G., *On Microscope Interferometry and the Specific Refraction Increment of a Crystalline Protein*. Journal of Histochemistry & Cytochemistry, 1958. 6(6): p. 393-393.

(21) Barer, R. and S. Joseph, *Refractometry of Living Cells. 3. Technical and Optical Methods*. Quarterly Journal of Microscopical Science, 1955. 96(4): p. 423-447.

(22) Grampp, W., O. Hallen, and B. Rosengren, *Mass Determination by Interference Microscopy and X-Ray Microscopy—a Comparative Study*. Experimental Cell Research, 1960. 19(3): p. 437-442.

(23) Gamble, C. N. and D. Glick, *Determination of the Total Dry Mass of Human Erythrocytes by Interference Microscopy and X-Ray Microradiography*. Journal of Histochemistry & Cytochemistry, 1960. 8(5): p. 332-333.

(24) Ottoson, R., K. Kahn, and D. Glick, Studies in Histochemistry. 48. *Dry Mass of Mast Cells Measured by Interference Microscopy and X-Ray Absorption*. Experimental Cell Research, 1958. 14(3): p. 567-574.

(25) Ruch, F. and G. F. Bahr, *Dry Mass Determination by Interference Microscopy Agreement with Quantitative Electron Microscopy*. Experimental Cell Research, 1970. 60(3): p. 470-&.

(26) Magnani, M., L. Rossi, V. Stocchi, L. Cucchiarini, G. Piacentini, and G. Fornaini, *Effect of Age on Some Properties of Mice Erythrocytes*. Mechanisms of Ageing and Development, 1988. 42(1): p. 37-47.

(27) Mysliwski, A. and P. Lass, *Increase of Size and Dry Mass of Mouse Erythrocytes Depending on Age of Donors*. Mechanisms of Ageing and Development, 1985. 29(2): p. 107-110.

(28) Nie, Z., F. Cui, Y. K. Tzeng, H. C. Chang, M. Chu, H. C. Lin, C. H. Chen, H. H. Lin, and A. L. Yu, *High-speed mass analysis of whole erythrocytes by charge—detection quadrupole ion trap mass Spectrometry*. Analytical Chemistry, 2007. 79: p. 7401-7407.

(29) Vaysse, J., R. Vassy, V. Eclache, D. Bladier, L. Gattegno, and P. Pilardeau, *Does Red Blood-Cell Size Correlate with Red Blood-Cell Age in Mouse*. Mechanisms of Ageing and Development, 1988. 44(3): p. 265-276.

(30) Wirth-Dzieciolowska, E., J. Karaszewska, K. Pysniak, M. Smolinska, and M. Gajewska, *Selected peripheral blood cell parameters in twelve inbred strains of laboratory mice*. Animal Science Papers and Reports, 2009. 27(1): p. 69-77.

(31) Barer, R., *Refractometry and Interferometry of Living Cells*. Journal of the Optical Society of America, 1957. 47(6): p. 545-556.

(32) Dawson, D. W., J. S. Hong, R. R. Shen, S. W. French, J. J. Troke, Y. Z. Wu, S. S. Chen, D. Gui, M. Regelson, Y. Marahrens, H. C. Morse, J. Said, C. Plass, and M. A. Teitell, *Global DNA methylation profiling reveals silencing of a secreted form of Epha7 in mouse and human germinal center B-cell lymphomas*. Oncogene, 2007. 26(29): p. 4243-4252.

(33) Lee, J. Y., M. Koi, E. J. Stanbridge, M. Oshimura, A. T. Kumamoto, and A. P. Feinberg, *Simple Purification of Human-Chromosomes to Homogeneity Using Muntjac Hybrid-Cells*. Nature Genetics, 1994. 7(1): p. 29-33.

(34) Shaffer, A. L., M. ShapiroShelef, N. N. Iwakoshi, A. H. Lee, S. B. Qian, H. Zhao, X. Yu, L. M. Yang, B. K. Tan, A. Rosenwald, E. M. Hurt, E. Petroulakis, N. Sonenberg, J. W. Yewdell, K. Calame, L. H. Glimcher, and L. M. Staudt, *XBP1, downstream of Blimp-1, expands the secretory apparatus and other organelles, and increases protein synthesis in plasma cell differentiation*. Immunity, 2004. 21(1): p. 81-93.

(35) Brewer, J. W. and J. A. Diehl, *PERK mediates cell-cycle exit during the mammalian unfolded protein response*. Proceedings of the National Academy of Sciences of the United States of America, 2000. 97(23): p. 12625-12630.

(36) Brewer, J. W., L. M. Hendershot, C. J. Sherr, and J. A. Diehl, *Mammalian unfolded protein response inhibits cyclin D1 translation and cell-cycle progression*. Proceedings of the National Academy of Sciences of the United States of America, 1999. 96(15): p. 8505-8510.

Example 2: Quantifying Real-Time Drug Sensitivity of Single and Clustered Breast Cancer Cells by Mass Profiling As discussed above, live cell mass profiling is a promising new approach for rapidly quantifying responses to therapeutic agents through picogram-scale changes in cell mass over time. A significant barrier in mass profiling is the inability of existing methods to handle pleomorphic cellular clusters and clumps, which are more commonly present in patient-derived samples or tissue cultures than are isolated single cells. Here, evidence is provided of automated Live Cell Interferometry (aLCI) as a rapid and accurate quantifier of the sensitivity of single cell and colony-forming human breast cancer cell lines to the HER2-directed monoclonal antibody, trastuzumab (Herceptin). Relative sensitivities were determined tens-to-hundreds of times faster than possible with traditional proliferation assays. These aLCI advances in clustered sample assessment and speed may be used for therapeutic response testing of patient-derived solid tumor samples, which are viable only for short periods ex vivo and likely to be in the form of cell aggregates and clusters.

In the United States in 2011, 230,480 women were diagnosed with breast cancer and 39,520 women died from the disease (see, e.g. R. Siegel, et al. *CA Cancer J Clin.* 2011, 61, 212-36). The clinical course and outcome for this common malignancy remains variable despite therapies that are usually guided by a combination of clinical assessments, including tumor subtype, clinical grade and stage, and the expression of estrogen (ER), progesterone (PR), and amplified HER2 cell surface receptors (see, e.g. M. Ignatiadis, et al. *Clin Cancer Res.* 2009, 15, 1848-52; M. Ignatiadis, et al. *Nat Rev Clin Oncol.* 2012, 9, 12-4). Unfortunately, breast cancers expressing ER, PR, and/or amplified HER2 surface receptors do not always respond to therapies that target these receptor-linked pathways, making the analysis of expression of these biomarkers alone insufficient for treatment decisions. For example, breast cancers with amplified HER2 expression frequently do not respond to the humanized monoclonal antibody trastuzumab (Herceptin) (see, e.g. J A. Wilken, et al. Primary trastuzumab resistance: new tricks for an old drug. In: Braaten D, editor. *Toward Personalized Medicine for Cancer* 2010. p. 53-65). Furthermore, initially responsive, receptor-positive tumors may become refractory to targeted therapies over time, which occurs for HER2-amplified breast cancers (see, e.g. R. Nahta, et al. *Breast Cancer Research.* 2006, 8) and many other types of cancer as well.

A common feature, and failure, of current biomarker approaches in breast and other cancers is their typically static, snapshot-in-time surrogate nature that does not directly evaluate tumor cell responses to particular agents for specific patients. A superior approach, if one was available, could be to rapidly determine by real-time monitoring how a tumor responds to a battery of candidate therapies and then to pick the agent(s) that are most efficacious for that particular patient's disease. Real-time mass profiling of living cells is a new and reproducible biophysical measurement modality that may provide a superior approach. Live cell mass profiling is accomplished primarily using optical methods (see, e.g. G. Popescu, et al. *American Journal of Physiology-Cell Physiology.* 2008, 295, C538-C44; B. Rappaz, et al. *Optics Express.* 2005, 13, 9361-73; J. Reed, et al. *Biophys J.* 2011, 101, 1025-31; J. Reed, et al. *ACS Nano.* 2008, 2, 841-6) or micro-fabricated sensors (see, e.g. M. Godin, et al. *Applied Physics Letters.* 2007; 91; K. Park, et al. *Proc Natl Acad Sci USA.* 2010, 107, 20691-6) and can yield rapid, continuous quantification of single-cell dry mass changes in a population of cells exposed to a changing external environment, including the detection of cellular responses to growth-inhibiting or cytotoxic agents (see, e.g. J. Reed, et al. *Biophys J.* 2011, 101, 1025-31). Unfortunately, due to technical limitations, live cell mass profiling has been constrained to cell types that exist as spatially isolated single cells, such as bacteria, yeasts, and lymphocytes. This is a substantial roadblock to the effective use of mass profiling for solid tumor therapeutic response testing, such as in breast cancer. In general, dissected solid tumor samples even when mechanically disaggregated exist as a combination of small and large multi-cellular clumps, sheets, or spheres, rather than as purely single cells. Also, the agitation required to separate solid tumors into single cells may damage the cells and disrupts the cell-cell and cell-matrix interactions which may be crucial to maintenance of the malignant phenotype and required to assess agent responsiveness (see, e.g. BE. Miller, et al. *Cancer Res.* 1981, 41, 4378-81; MS. Wicha, et al. *Proc Natl Acad Sci USA.* 1982, 79, 3213-7).

Using a mass profiling approach as disclosed herein, termed automated Live Cell Interferometry (aLCI), this inhibitory barrier has been overcome. With aLCI one has profiled the therapeutic response kinetics of breast cancers that grow in culture as both single cells and as large colonies or clusters. These organized colonies were up to 50 cells in size and much larger colonies may also be accurately measured. One has quantified the growth dynamics of populations of cells or colonies from four breast cancer cell lines exposed to trastuzumab over the course of six hours. In the study, aLCI was performed without prior knowledge of which breast cancer lines expressed amplified HER2 surface receptor or at what level. Trastuzumab-sensitive and resistant tumors were rapidly differentiated by quantifying single-cell/single-colony mass accumulation with very high precision. Notably, aLCI identified sensitive and resistant cells and colonies about a log-order more quickly than possible using traditional techniques, such as cell proliferation assays. This improvement in speed and sensitivity allows for assessing sensitive versus refractory HER2-amplified breast cancer responses. It also allows for translation to the clinic, where often fragile, patient derived cells are viable for short periods only and samples are most likely to be in the form of a heterogeneous mixture of single cells and aggregated clumps for many if not all solid tumor types.

Figure 13:
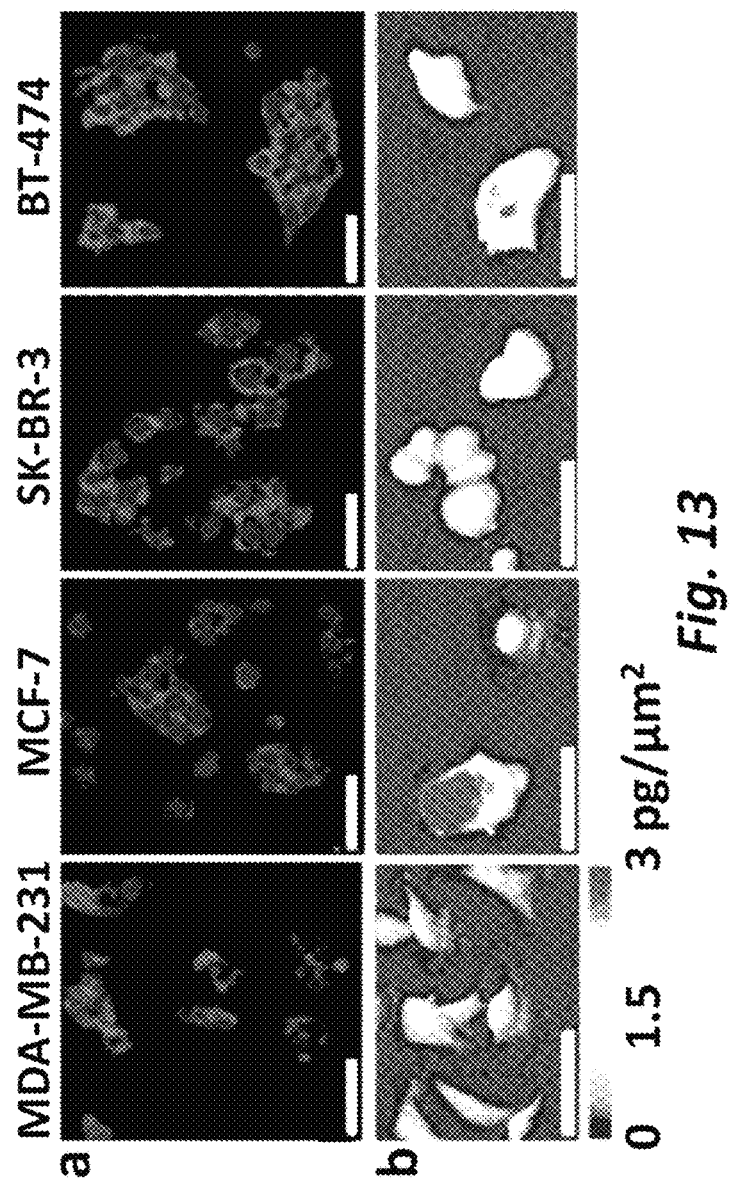
FIG. 13 illustrates various single cells, cell clusters, and dense colonies imaged and mass quantified by aLCI. (a) Confocal images of MDA-MB-231, MCF-7, SK-BR-3, and BT-474 breast cancer cell lines. SK-BR-3 and MDA-MB-231 cell lines grow as single cells or in loose clusters, whereas the BT-474 and MCF-7 cell lines grow as dense multi-cellular colonies. Red is Alexa 568 Phalloidin actin stain and blue is a DAPI nuclear stain. (b) Phase images of mass distributions for each cell line. Single cells, loose clusters, and dense colonies are reproducibly quantified in real-time with aLCI. Color scale denotes mass density in pg/um$^2$. Scale bars are 50 um.
Figure 14:
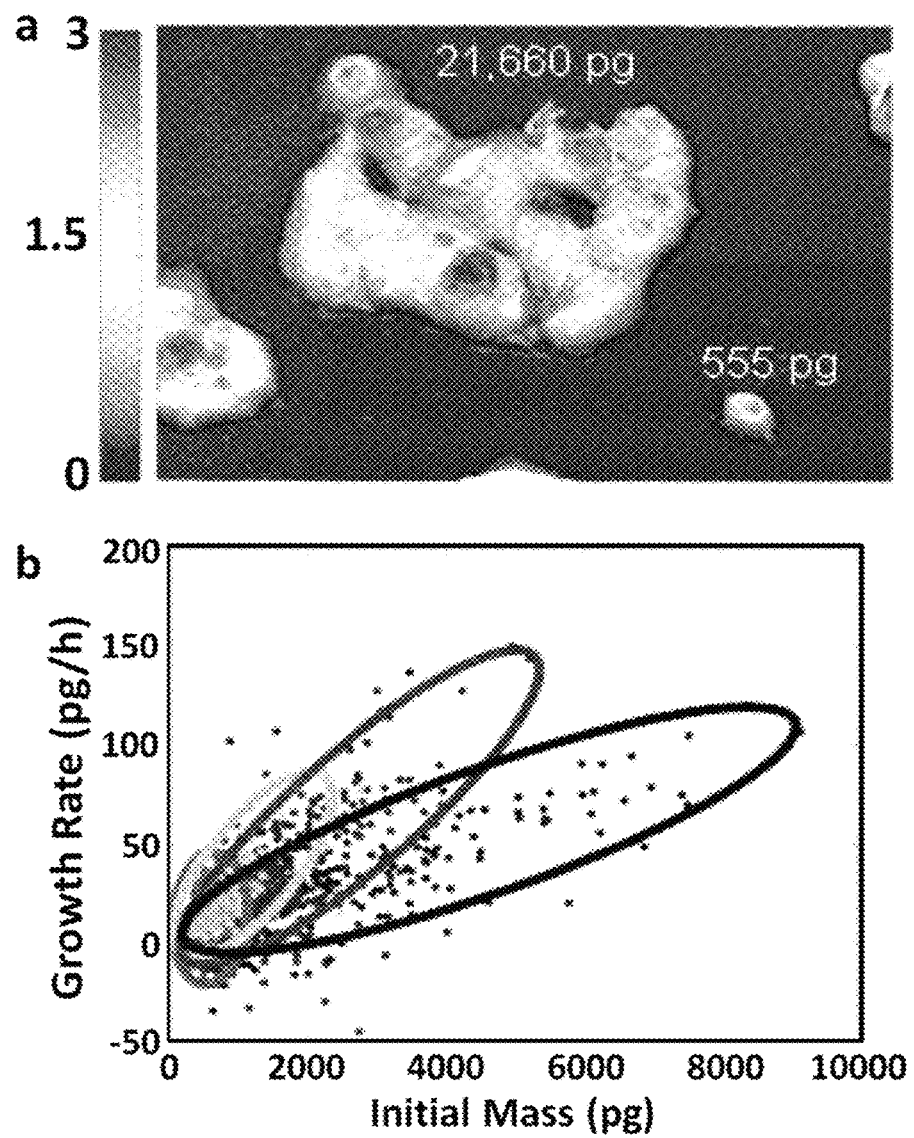
FIG. 14 illustrates simultaneous imaging of single cells and large colonies with aLCI. (a) The phase image shows a single MCF-7 cell (555 pg) alongside a multi-cellular MCF-7 colony (21,660 pg) consisting of approximately 52 cells. Color scale denotes mass density in pg/um$^2$. (b) Composite scatter plot of growth rate vs. initial mass for all cell lines. MDA-MB-231 (red), MCF-7 (blue), SK-BR-3 (cyan), and BT-474 (black) are overlaid to show the range of cell and colony sizes and growth rates of the different lines. Colony forming lines (MCF-7 and BT-474) span the range from a single cell to large, multi-cellular colonies.

Mass response profiling of four human breast cancer cell lines was performed in real-time using aLCI with co-incubation of 20 ug/ml clinical grade trastuzumab. For each cell type, a control well containing only culture media and a treated well containing trastuzumab were measured simultaneously. Two of the lines, BT-474 and SK-BR-3, have amplified HER2 with high level surface receptor expression and are differentially sensitive to trastuzumab in vitro as assessed by 5-7 day proliferation assays, whereas the other two lines, MCF-7 and MDA-MB-231, express the HER2 receptor at normal levels and are trastuzumab resistant (see, e.g. N A. O'Brien, et al. *Molecular Cancer Therapeutics.* 2010, 9, 1489-502). Importantly, these cell lines grow with very different morphologies. MDA-MB-231 and SK-BR-3 lines grow as single cells or in loose disaggregated clusters, whereas MCF-7 and BT-474 lines grow as dense multi-cellular colonies (FIG. 13). The relative scale between a single MCF-7 cell (mass~$5 \times 10^2$ pg) and a large colony (~$22 \times 10^3$ pg) covers a 44-fold difference in mass (FIG. 14).

Figure 15:
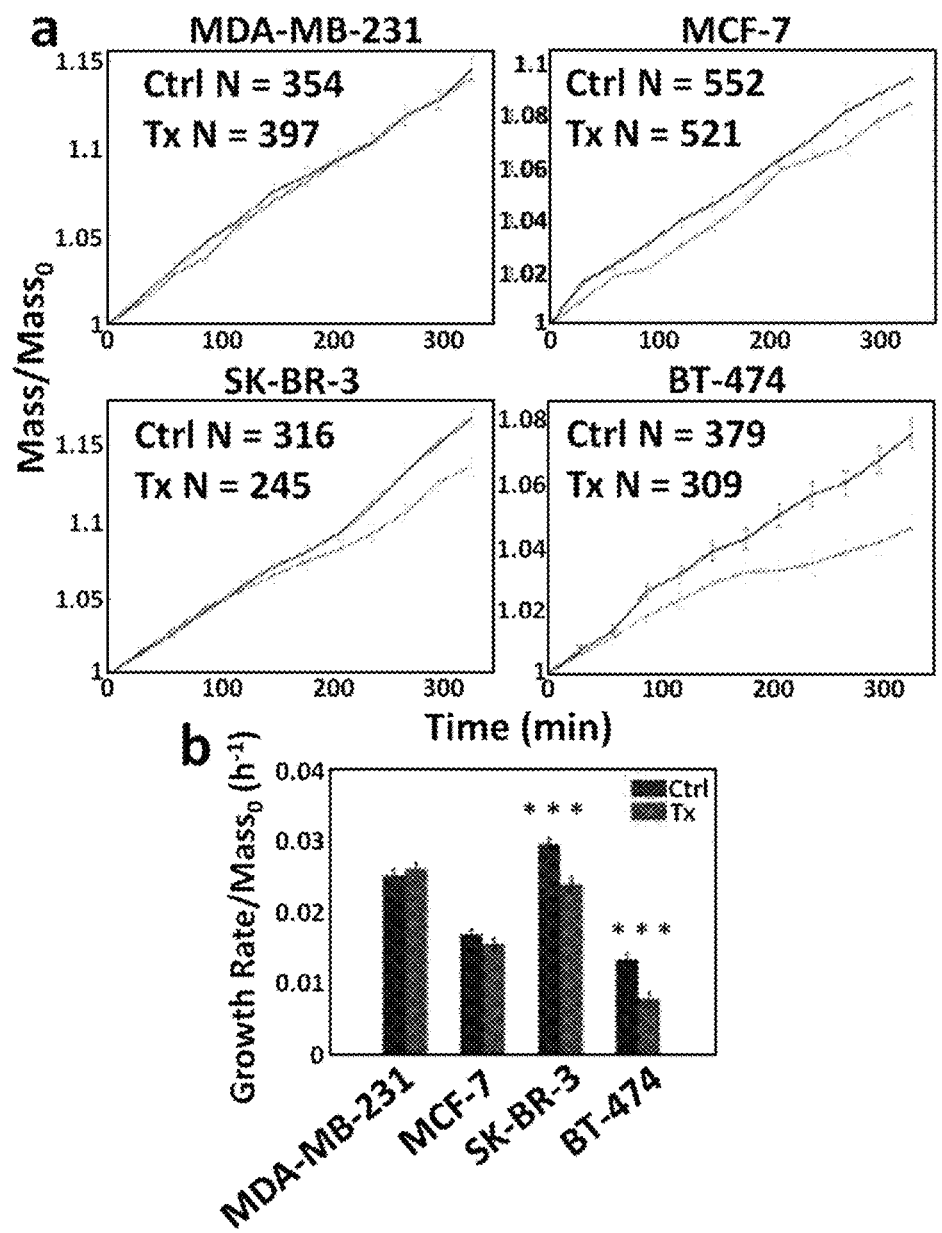
FIG. 15 illustrates breast cancer cell growth inhibition due to trastuzumab reproducibly quantified with aLCI within 3-5 h. (a) Population mean normalized mass versus time plots for each cell line with 20 ug/ml trastuzumab treatment (error bars indicate standard error). (b) Growth inhibition due to trastuzumab treatment becomes highly significant (p<0.001) for the SKBR-3 and BT-474 lines by 7 h. Hourly growth rates are calculated from a linear fit to mass accumulation data.

The masses of hundreds of individual cells and colonies were quantified continuously over 7 h. Mean mass accumulation rates for each cell line at 30 min intervals were plotted to characterize the whole population response in the treated and control groups (FIG. 15a). Treated and control samples of HER2 normal expression lines, MCF-7 and MDA-MB-231, exhibited an identical increase in mass over time. In contrast, the growth rates of treated and control samples for HER2 amplified high-expressing lines, BT-474 and SK-BR-3, began to diverge at ~4 h of treatment. Trastuzumab sensitive lines, SK-BR-3 and BT-474, showed a highly significant difference ($p<0.001$) in growth rates whereas insensitive lines, MCF-7 and MDA-MB-231, showed no significant difference (FIG. 15b). The BT-474 line was more responsive to trastuzumab than was the SK-BR-3 line, with control-to-treated mass fold changes of 1.70+/−0.39 and 1.24+/−0.10 respectively after 6 h (mean+/−standard error; FIG. 16). Of the two sensitive lines, SK-BR-3 exists primarily as isolated single cells whereas BT-474 grows in small colonies, indicating that colony formation is not predictive or required for trastuzumab sensitivity or resistance. One also compared the aLCI-measured response to trastuzumab to that determined with traditional multi-day, cell counting growth-inhibition assays. In all four cases, the trastuzumab sensitivity measured by aLCI over 6 h was concordant with that measured by cell counting over 3-7 days (FIG. 16).

These results show that live cell mass quantification via aLCI can rapidly and sensitively detect the biologic response to trastuzumab in breast cancer regardless of the physical configuration or association of the cells being examined. Other recently-developed live cell mass profiling methods, such as MEMS micro-resonators, can measure the mass of single cells instantaneously with high accuracy, depending on the configuration of the micro-resonator (see, e.g. M. Godin, et al. *Applied Physics Letters*. 2007; 91; K. Park, et al. *Proc Natl Acad Sci USA*. 2010, 107, 20691-6). A drawback to that approach is that in order to achieve sufficient sensitivity, the active area of the resonator must be on the order of microns or smaller, which makes the continuous measurement of mixtures of single cells and larger multicellular colonies, as occurs for most solid tumor types, very difficult if not impossible.

In general, quantitative phase optical microscopy approaches, including aLCI, possesses mass measurement precision and accuracy on par with MEMS-based approaches, (see, e.g. G. Popescu, et al. *American Journal of Physiology-Cell Physiology*. 2008, 295, C538-C44; J. Reed, et al. *Biophys J*. 2011, 101, 1025-31) and their application to the study of cell clusters and clumps has been limited by practical difficulties associated with high throughput phase imaging, rather than by fundamental physical limitations. Converting a raw phase image into mass information can be computationally challenging, particularly in the case of clusters of cells and objects with complex internal structures and optical thicknesses that are large compared to the illumination wavelength (see, e.g. D. Ghiglia, et al. *Two-Dimensional Phase Unwrapping: Theory, Algorithms, and Software*: John Wiley & Sons; 1998). The increased speed of analysis and quantification of therapeutic responses for aggregated cell clumps, sheets, and spheres provides exciting new opportunities for agent selection and prognosis in solid tumor therapy.

Materials & Methods
Cell Lines and Culture

BT-474, SK-BR-3, MDA-MB-231, and MCF-7 breast cancer cell lines were obtained from American Type Culture Collection (Rockville, Md.). All lines were maintained in RPMI 1640 (Cellgro; Manassas, Va.) growth media supplemented with 10% fetal bovine serum (Omega; Tarzana, Calif.) and 1% penicillin, streptomycin, and L-glutamine.
Drug Treatment Clinical grade trastuzumab (Herceptin) (Genentech; South San Francisco, Calif.) was used at 20 ug/ml.
Proliferation Assays $5\times10^4$ cells were seeded into 12-well plates and allowed to adhere and grow for 2 days before beginning treatment. On days 0, 3, 5, and 7 of treatment with 20 ug/ml Herceptin, cells were trypsinized and counted. To calculate the fold change, the doubling time was determined ($DT=t*(\log(2)/\log(N_t/N_0))$) for control and drug treated samples and the fold change taken as $DT_{drug}/DT_{ctrl}$. DT=doubling time, t=time, $N_t$=number or mass of cells at time t, $N_0$=number or mass of cells at time t=0.
Confocal Imaging Cells were seeded onto chambered coverglass and allowed to adhere overnight. Cells were fixed with 3.7% formaldehyde in 1×PBS, pH 7.4, and permeablized in 0.1% Triton-X. Samples were then incubated with Alexa 568-Phalloidin actin stain (Invitrogen; Grand Island, N.Y.) and DAPI. Confocal images were taken with a Zeiss LSM 780 CCD camera using Zen 2010 software.
Interferometer The live cell interferometer has been described previously (see, e.g. J. Reed, et al. *Biophys J*. 2011, 101, 1025-31; J. Reed, et al. *ACS Nano*. 2008, 2, 841-6; J. Reed, et al. *Nanotechnology*. 2008, 19). The system consists of a modified Bruker NT9300 optical profiler (Bruker; Tucson, Ariz.) with a 20×0.28NA Michelson interference objective. The Michelson interferometer contains a beam splitter, reference mirror, and compensating fluid cell to account for the optical path differences induced by the fluid surrounding the sample. The phase shifting (PSI) method was used to capture phase images of the cell samples. To enable multi-sample imaging, aLCI employs a small motor to adjust the interferometer reference mirror for small differences in cover glass optical path length at each sample well.
Data Analysis Image analysis was performed using a custom, multi-step program written in Matlab (Mathworks Inc., Natick, Mass.). The first step was a phase-unwrapping step to remove phase-errors (integer wavelength errors due to the ambiguity inherent in quantitative phase imaging) which remained after processing by the Goldstein phase unwrapping algorithm employed by Bruker Vision software (Bruker Nano Inc., Tucson, Ariz.). This algorithm uses multiple random walks away from each pixel to remove integer wavelength jumps and non-physical excursions below background level. The second step is to segment each image into cell or colony objects using a combination of a local adaptive median filter and a watershed transform. Finally, objects identified by image segmentation were tracked using the particle tracking code adapted for Matlab by Daniel Blair and Eric Dufresne, based on an IDL particle tracking code (see, e.g. J C. Crocker, et al. *Journal of Colloid and Interface Science*. 1996, 179, 298-310).

The invention claimed is:

1. A method for measuring a cellular response to an environment comprising:
   (a) placing a test cell in a first environment;
   (b) using an interference microscope to perform live cell interferometry and thereby determine a measure proportional to the mass of said test cell, where said live cell interferometry comprises measuring the fractional phase shift between a test beam of light propagating through said test cell and a reference beam of light with said interference microscope and integrating said phase shift over the area of said test cell to provide said measure proportional to the mass of said test cell;

(c) placing a reference cell in a second environment;

(d) using an interference microscope to perform live cell interferometry and thereby determine a measure proportional to the mass of said reference cell, where said live cell interferometry comprises measuring the fractional phase shift between a test beam of light propagating through said reference cell and a reference beam of light with said interference microscope and integrating said phase shift over the area of said reference cell to provide said measure proportional to the mass of said reference cell; and (e) determining the difference between the measure determined in (b) and the measure determined in (d) to thereby provide a measure of the change in mass of said test cell in response to the first environment.

2. The method of claim 1, wherein said test cell is present in the first environment as an isolated single cell.

3. The method of claim 1, wherein said test cell is present in the first environment in a cluster or clump of cells.

4. The method of claim 1, wherein mass properties of a plurality of test cells present in the first environment are observed.

5. The method of claim 1, wherein the first environment comprises a test composition and the second environment does not comprise the test composition.

6. The method of claim 5, wherein the test composition comprises an antibiotic, an antibody, an alkylating agent, an antimetabolite, a cell cycle inhibitor, a topoisomerase inhibitor, an siRNA or a cell.

7. The method of claim 6, wherein the test composition comprises an antibody that binds HER2.

8. The method of claim 5, wherein said method comprises determining the measure proportional to the mass of the test cell in the first environment a plurality of times to thereby measure changes in the mass property of the cell over a period of time.

9. The method of claim 8, wherein changes in said measure proportional to the mass of the test cell are observed over time to thereby determine a temporal mass profile.

10. The method of claim 9, further comprising comparing said temporal mass profile to a database of temporal mass profiles, wherein the database of temporal mass profiles is selected to include temporal mass profiles that are characteristic of cellular sensitivity to the test composition and temporal mass profiles that are characteristic of cellular resistance to the test composition.

11. The method of claim 1, wherein the mass of the test cell is determined from said measure proportional to the mass of a test cell using an equation:

$$m = i/\alpha \int \varphi \lambda \, dA$$

wherein m is the mass of the cell, $\alpha$ is a constant describing a relationship between the phase shift and cell mass, $\varphi$ is the measured fractional phase shift, $\lambda$ is the illumination wavelength, and integration is performed across an entire cell area, A.

12. The method of claim 11, wherein $\alpha = 1.8 \times 10^{-3}$ m$^3$ kg$^{-1}$.

13. The method of claim 11, wherein said interference microscope comprises:
   a detector operatively coupled to the microscope;
   a sample assembly comprising an observation chamber that contains said test cell;
   a reference assembly comprising a reference chamber that contains said reference cell; and
   a beam splitter for splitting a light beam from a light source into a test beam and a reference beam.

14. The method of claim 13, wherein the observation chamber comprises at least one perfusion conduit that circulates a cell media within the observation chamber.

* * * * *